(12) United States Patent
Cook

(10) Patent No.: US 7,160,996 B1
(45) Date of Patent: Jan. 9, 2007

(54) FLUORESCENCE ENERGY TRANSFER PROBES WITH STABILIZED CONFORMATIONS

(75) Inventor: Ronald M. Cook, Novato, CA (US)

(73) Assignee: Bioresearch Technologies, Inc., Novato, CA (US)

( * ) Notice: Subject to any disclaimer, the term of this patent is extended or adjusted under 35 U.S.C. 154(b) by 0 days.

(21) Appl. No.: 09/591,185

(22) Filed: Jun. 8, 2000

Related U.S. Application Data

(60) Provisional application No. 60/138,376, filed on Jun. 9, 1999.

(51) Int. Cl.
*C07H 21/04* (2006.01)

(52) U.S. Cl. .............. 536/24.3; 536/24.31; 536/24.32

(58) Field of Classification Search ............ 435/6, 435/5, 91.1, 93.1, 91.2; 536/24.3, 26.6, 23.1, 536/24.33, 22.1, 25.3, 25.32
See application file for complete search history.

(56) References Cited

U.S. PATENT DOCUMENTS

| | | | |
|---|---|---|---|
| 5,753,436 A | 5/1998 | Bronstein et al. ............. 435/6 |
| 5,760,201 A | 6/1998 | Glazer et al. ............. 536/22.1 |
| 5,763,189 A | 6/1998 | Buechler et al. ............. 435/7.1 |
| 5,824,473 A * | 10/1998 | Meade et al. ................. 435/6 |
| 5,866,336 A * | 2/1999 | Nazarenko et al. ............ 435/6 |
| 5,945,283 A | 8/1999 | Kowk et al. ................... 435/6 |
| 6,114,518 A | 9/2000 | Pitner et al. |
| 6,153,737 A * | 11/2000 | Manoharan et al. ........ 536/22.1 |

OTHER PUBLICATIONS

NS Templeton et al., Nature Biotechnology, "Improved DNA: liposome complexes for increased systemic delivery and gene expression," Jul. 1997, vol. 15, pp. 647-651.*

Templeton, et al. "Improved DNA: Lipsome Complexes for Increased Systemic Delivery and Gene Express" *Nature Biology* Jul. 1997, vol. 15, pp. 647-652.

* cited by examiner

*Primary Examiner*—Janet L. Epps-Ford
(74) *Attorney, Agent, or Firm*—Morgan Lewis & Bockius LLP

(57) ABSTRACT

The present invention provides a class of Conformationally Assisted Probes comprising (a) a nucleic acid moiety; (b) an energy donor moiety; (c) an energy acceptor moiety; and (d) one or more stabilizing moieties.

12 Claims, 9 Drawing Sheets

Fluorescein=FAM

Tamra=TAM

Cholesterol

5' Nuclease Assay PCR Cycle

Polymerization

Strand Displacement

Probe Digestion

Cycle Complete

FIG. 5

FLUORESCENCE ENERGY TRANSFER PROBES WITH STABILIZED CONFORMATIONS

CROSS-REFERENCE TO RELATED APPLICATIONS

This application claims the benefit of U.S. Provisional Application No. 60/138,376, filed on Jun. 9, 1999, the disclosure of which is incorporated herein in its entirety for all purposes.

BACKGROUND OF THE INVENTION

Fluorescent oligonucleotide probes are important tools for genetic analysis, in both genomic research and development, and in clinical medicine. As information from the Human Genome Project accumulates, the level of genetic interrogation mediated by fluorescent probes will expand enormously. One particularly useful class of fluorescent probes are self quenching probes, also known as fluorescence energy transfer probes, or FET probes. Although the design of different probes using this motif may vary in detail, FET probes contain both a fluorophore and quencher tethered to an oligonucleotide. The fluorophore and the quencher are configured to produce a signal only as a result of hybridization to an intended target. Despite the limited availability of FET probes, techniques incorporating their use are rapidly displacing competitive methods.

Probes containing a fluorophore-quencher pair have been developed for hybridization assays where the probe forms a hairpin structure, i.e., where the probe hybridizes to itself to form a loop such that the quencher molecule is brought into proximity with the reporter molecule in the absence of a complementary nucleic acid sequence to prevent the formation of the hairpin structure (see, for example, WO 90/03446; European Patent Application No. 0 601 889 A2). When a complementary target sequence is present, hybridization of the probe to the complementary target sequence disrupts the hairpin structure and causes the probe to adopt a conformation where the quencher molecule is no longer close enough to the reporter molecule to quench the reporter molecule. As a result, the probes provide an increased fluorescent signal when hybridized to a target sequence than when they are unhybridized. Probes including a hairpin structure can be difficult to design and may interfere with the hybridization of the probe to the target sequence.

Assays have also been developed for identifying the presence of a hairpin structure using two separate probes, one containing a reporter molecule and the other a quencher molecule (see, Meringue, et al., *Nucleic Acids Research*, 22: 920–928 (1994)). In these assays, the fluorescence signal of the reporter molecule decreases when hybridized to the target sequence due to the quencher molecule being brought into proximity with the reporter molecule.

One particularly important application for probes including a reporter—quencher molecule pair is their use in nucleic acid amplification reactions, such as polymerase chain reactions (PCR), to detect the presence and amplification of a target nucleic acid sequence. In general, nucleic acid amplification techniques have opened broad new approaches to genetic testing and DNA analysis (see, for example, Arnheim et al. *Ann. Rev. Biochem.*, 61: 131–156 (1992)). PCR, in particular, has become a research tool of major importance with applications in, for example, cloning, analysis of genetic expression, DNA sequencing, genetic mapping and drug discovery (see, Arnheim et al., supra; Gilliland et al., *Proc. Natl. Acad. Sci. USA*, 87: 2725–2729 (1990); Bevan et al., *PCR Methods and Applications*, 1: 222–228 (1992); Green et al., *PCR Methods and Applications*, 1: 77–90 (1991); Blackwell et al., *Science*, 250: 1104–1110 (1990)).

Commonly used methods for detecting nucleic acid amplification products require that the amplified product be separated from unreacted primers. This is typically achieved either through the use of gel electrophoresis, which separates the amplification product from the primers on the basis of a size differential, or through the immobilization of the product, allowing free primer to be washed away. However, three methods for monitoring the amplification process without prior separation of primer have been described. All of them are based on FRET, and none of them detect the amplified product directly. Instead, all three methods detect some event related to amplification. For that reason, they are accompanied by problems of high background, and are not quantitative, as discussed below.

One method, described in Wang et al. (U.S. Pat. No. 5,348,853; Wang et al., *Anal. Chem.*, 67: 1197–1203 (1995)), uses an energy transfer system in which energy transfer occurs between two fluorophores on the probe. In this method, detection of the amplified molecule takes place in the amplification reaction vessel, without the need for a separation step. This method, however, does not detect the amplified product, but instead detects the dissociation of primer from the "energy-sink" oligonucleotide. Thus, this method is dependent on detection of a decrease in emissions; a significant portion of labeled primer must be utilized in order to achieve a reliable difference between the signals before and after the reaction.

A second method detecting an amplification product without prior separation of primer and product is the 5'-nuclease PCR assay (also referred to as the TaqMan™ assay) (Holland et al., *Proc. Natl. Acad. Sci. USA*, 88: 7276–7280 (1991); Lee et al., *Nucleic Acids Res.*, 21: 3761–3766 (1993)). This assay detects the accumulation of a specific PCR product by hybridization and cleavage of a doubly labeled fluorogenic probe (the "TaqMan" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

In the TaqMan assay, the donor and quencher are preferably located on the 3'- and 5'-ends of the probe, because the requirement that 5'-3 hydrolysis be performed between the fluorophore and quencher may be met only when these two moieties are not too close to each other (Lyamichev et al., *Science*, 260:778–783 (1993). This requirement is a serious drawback of the assay as the efficiency of energy transfer decreases with the inverse sixth power of the distance between the reporter and quencher. Thus, if the quencher is not close enough to the reporter to achieve the most efficient quenching the background emissions from unhybridized probe can be quite high.

Yet another method of detecting amplification products that relies on the use of energy transfer is the "beacon probe" method described by Tyagi et al. (*Nature Biotech.*, 14:303–309 (1996)) which is also the subject of U.S. Pat. Nos. 5,119,801 and 5,312,728 to Lizardi et al. This method employs oligonucleotide hybridization probes that can form hairpin structures. On one end of the hybridization probe (either the 5'- or 3'-end) there is a donor fluorophore, and on the other end, an acceptor moiety. In this method, the acceptor moiety is a quencher, absorbing energy from the donor. Thus when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce. As a result, the amount of fluorescence will increase as the amount of PCR product increases, and thus can be used as a measure of the progress of the PCR.

Because this method is based on hybridization of the probe to a template region between the primer sequences, it has a number of problems associated with it. For example, it is unlikely that the beacon probes will hybridize quantitatively to one strand of double-stranded PCR product, especially when the amplification product is much longer than the beacon probe.

Additional limitations have also impeded the application and use of FET probes. First, currently available probe designs have a higher fluorescent noise background than is desirable. In some cases this is due to the difficulty of purifying the probe which must be rigorously purged of any spurious fluorescent byproducts. As a result probes must undergo at least 2 levels of purification before they are acceptable. This labor factor results in very high probe cost, approximately $300–$600 per probe. A second fundamental limitation is the inherent noise of the probe itself which is a result of the physical geometry of the probe which places constraints on the fluorophore and quencher interaction.

In view of the deficiencies in current FET probes, there exists in the art a need for improved probes for detecting nucleic acids (e.g., amplification products) rapidly, sensitively, reliably and quantitatively. Ideal probes would give rise to minimal background signal and be easily and inexpensively prepared. Quite surprisingly, the present invention provides such probes

SUMMARY OF THE INVENTION

The present invention provides a new class of fluorescence energy transfer probes with optimized characteristics for genetic detection, discrimination and quantitation. These probes preferably have, at one or both oligonucleotide termini, an appendant ligand having a weak affinity for another component of the probe. The interaction of this ligand with another probe component favors conformations that result in enhanced interaction of the donor/acceptor pair and subsequently in lower noise and higher detection sensitivity. In accordance with their behavior, these probes are termed Conformationally Assisted Probes, or CAPs. CAP probes are useful as detection agents in a variety of DNA amplification/quantification strategies including 5'-nuclease assay (PCR-Taqman), Strand Displacement Amplification (SDA), Nucleic Acid Sequence-Based Amplification (NASBA), Rolling Circle Amplification (RCA), as well as for direct detection of targets in solution phase or solid phase (e.g., array) assays. Moreover, CAP probes have properties that allow them to be more economically manufactured than present probes.

The probes of the invention are unhindered by many of the deficiencies of existing FET probes. Moreover, they possess characteristics that are optimized for genetic detection, discrimination and quantitation. These probes utilize a novel conformationally assisted approach to eliminate background probe signal. In addition, contrary to known FET probes which are difficult to purify and which cost more than $300 per probe, the present probes are quickly and easily purified to homogeneity. This enhanced ease of purification results in a lower cost per probe for CAPs than for existing FET probes.

Thus, in a first aspect, the present invention provides a CAP probe having a formula selected from:

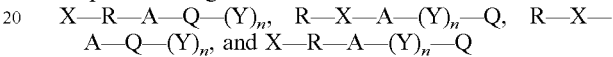

wherein, A is a nucleic acid chain comprising nucleic acid monomers selected from the group consisting of natural nucleic acids, modified nucleic acids and combinations thereof. R is a molecular energy transfer donor. Q is a molecular energy acceptor. X and Y are the same or different and are non-nucleotide stabilizing moieties that interact to bring R and Q into operative proximity, thereby enabling transfer of energy from R to Q. The subscript n is 0 or 1.

In another aspect, the invention provides a CAP probe having the formula:

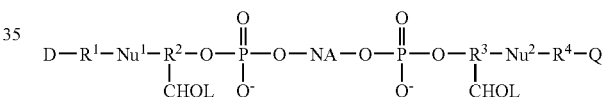

in which, CHOL is a cholesterol derivative. $R^1$, $R^2$, $R^3$ and $R^4$ are linker moieties independently selected from the group consisting of substituted or unsubstituted alkyl and substituted or unsubstituted heteroalkyl. $Nu^1$ and $Nu^2$ are independently selected nucleotide residues and NA is a nucleic acid. D is a donor of light energy and Q is a quencher of light energy.

In a third aspect, the invention provides a CAP probe having the formula:

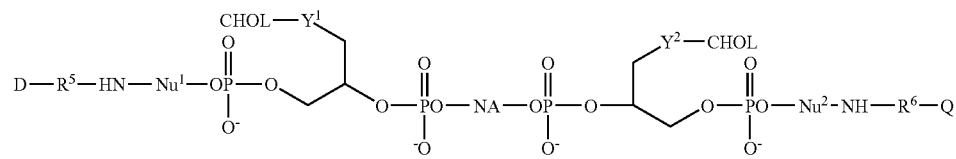

in which, NA is a nucleic acid sequence. $Nu^1$ and $Nu^2$ are independently selected nucleotide residues. $Y^1$ and $Y^2$ are linking groups independently selected from the group consisting of substituted or unsubstituted alkyl and substituted or unsubstituted heteroalkyl. $R^5$ and $R^6$ are linking groups independently selected from the group consisting of substituted or unsubstituted alkyl and substituted or unsubstituted heteroalkyl. D is a donor of light energy and Q is a quencher of light energy.

Other objects and advantages of the present invention will be apparent from the detailed description and examples that follow.

BRIEF DESCRIPTION OF THE DRAWINGS

FIG. 5 is a schematic diagram of a 5'-nuclease assay PCR cycle.

DETAILED DESCRIPTION OF THE INVENTION AND THE PREFERRED EMBODIMENTS

Abbreviations

Figure 1A:
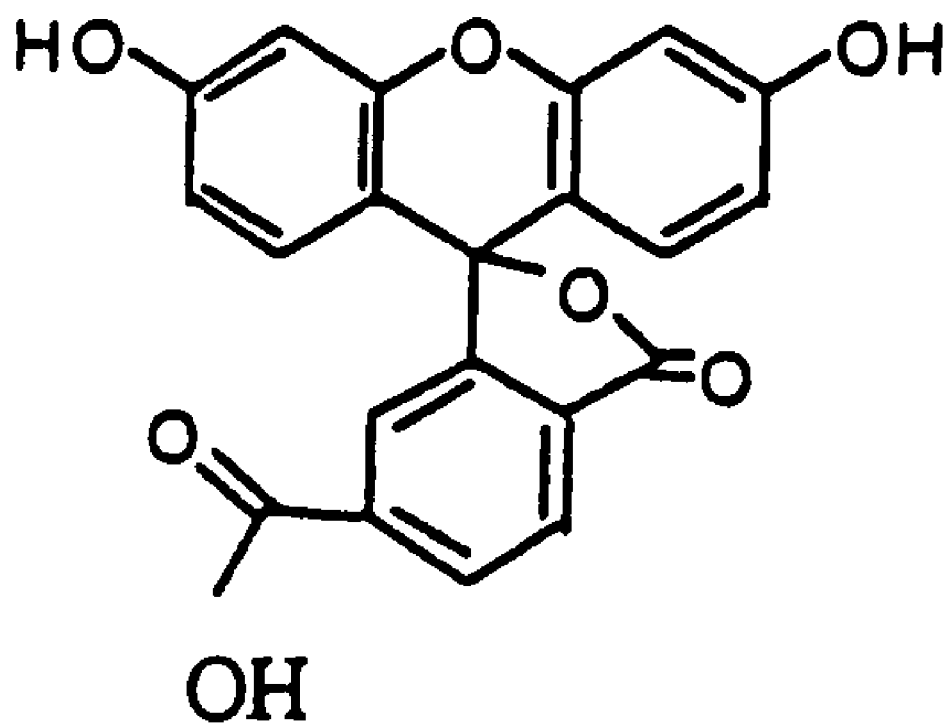
FIG. 1 is a schematic diagram of the structure of a CAP of the invention and its constituents: (A) is an exemplary donor (FAM); (B) is an exemplary acceptor (TAMRA); and (C) is an exemplary stabilizing moiety (CHOL).
Figure 1B:
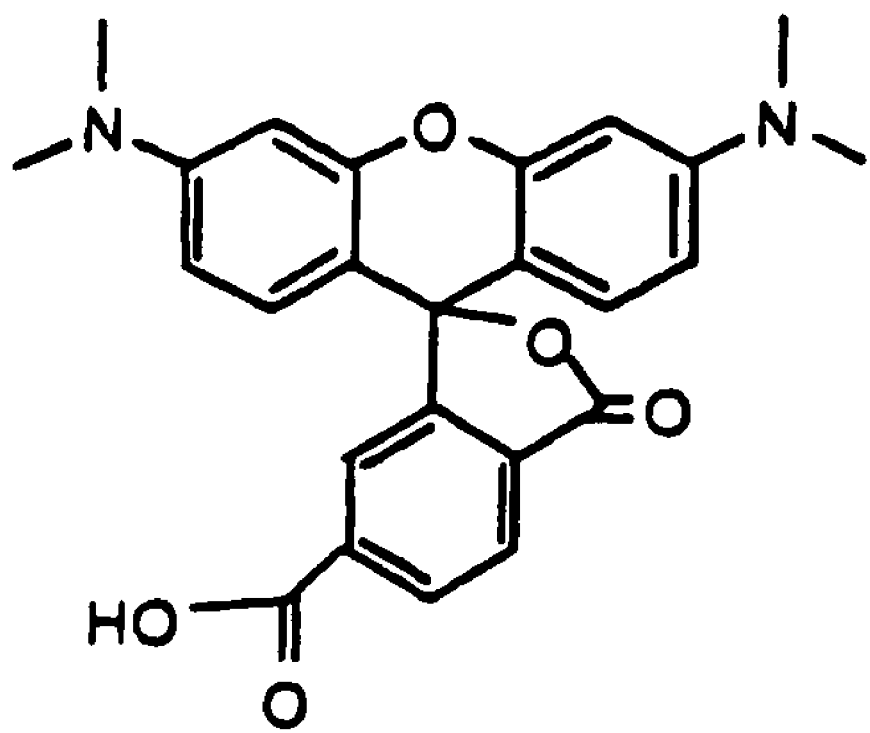
Figure 1C:
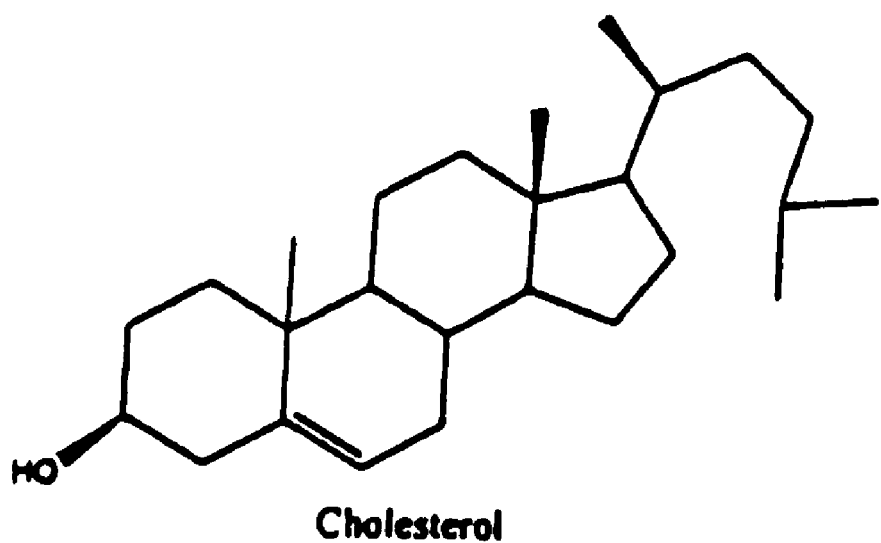

"MET," as used herein, refers to "Molecular Energy Transfer." MET is a generic term that encompasses the transfer of energy from one molecule or portion of a molecule to another. Examples of MET include, but are not limited to, transfer of nuclear magnetic resonance energy and transfer of light energy (e.g., Fluorescence Energy Transfer).

"FET," as used herein, refers to "Fluorescence Energy Transfer." "FRET," as used herein, refers to "Fluorescence Resonance Energy Transfer." These terms are used herein to refer to both radiative and non-radiative energy transfer processes. For example, processes in which a photon is emitted and those involving long range electron transfer are included within these terms. Throughout this specification, both of these phenomena are subsumed under the general term "donor-quencher energy transfer."

"BHQ" as used herein, refers to a genus of dark quenchers known as Black Hole Quenches.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

"Analyte", as used herein means any compound or molecule of interest for which a diagnostic test is performed. An analyte can be, for example, a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc., without limitation.

As used herein, "energy transfer" refers to the process by which the excited state energy of an excited group is altered by a modifying group, such as a quencher. If the excited state energy-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena.

As used herein, "energy transfer pair" refers to any two molecules that participate in energy transfer. Typically, one of the molecules acts as a fluorescent group, and the other acts as a fluorescence-modifying group. The preferred energy transfer pair of the instant invention comprises a fluorescent group and a quenching group of the invention. There is no limitation on the identity of the individual members of the energy transfer pair in this application. All that is required is that the spectroscopic properties of the energy transfer pair as a whole change in some measurable way if the distance between the individual members is altered by some critical amount. "Energy transfer pair" is used to refer to a group of molecules that form a complex within which energy transfer occurs. Such complexes may include, for example, two fluorescent groups, which may be different from one another and one quenching group, two quenching groups and one fluorescent group, or multiple fluorescent groups and multiple quenching groups. In cases where there are multiple fluorescent groups and/or multiple quenching groups, the individual groups may be different from one another.

As used herein, "fluorescence-modifying group" refers to a molecule of the invention that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, and a change in fluorescence lifetime. One example of a fluorescence-modifying group is a quenching group.

As used herein, "quenching group" refers to any fluorescence-modifying group of the invention that can attenuate at least partly the light emitted by a fluorescent group. This attenuation is referred to herein as "quenching". Hence, illumination of the fluorescent group in the presence of the quenching group leads to an emission signal that is less intense than expected, or even completely absent. Quenching typically occurs through energy transfer between the fluorescent group and the quenching group.

As used herein, "nucleic acid" and olignucleotide means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a BHQ, a fluorophore or another moiety.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Bioactive species," refers to molecules that, when administered to an organism, affect that organism. Exemplary bioactive species include pharmaceuticals, pesticides, herbicides, growth regulators and the like. Bioactive species encompasses small molecules (i.e., approximately <1000 daltons), oligomers, polymers and the like. Also included are nucleic acids and their analogues, peptides and their analogues and the like.

The term "alkyl" is used herein to refer to a branched or unbranched, saturated or unsaturated, monovalent hydrocarbon radical, generally having from about 1–30 carbons and preferably, from 4–20 carbons and more preferably from 6–18 carbons. When the alkyl group has from 1–6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls," and "cyclic alkyl."

"Substituted alkyl" refers to alkyl as just described including one or more substituents such as, for example, lower alkyl, aryl, acyl, halogen (i.e., alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$H_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

"Organic functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Methods to prepare each of these functional groups are well-known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

Introduction

The present invention provides a new class of energy transfer probes of molecular structure and function. Termed "conformationally assisted probes," these species are more advantageous for many applications than previous energy transfer probes. Until the CAPs of the present invention became available, energy transfer probes were limited in the sequences of biomolecules that could be included as a recognition component of the probe. In a nucleic acid energy transfer probe, for example, the nucleic acid component was limited to those structures that, in their unhybridized states formed hairpins, loops, etc. to bring the donor and acceptor moieties within sufficient proximity to allow energy transfer to occur. In contrast to previous probes, the CAPs of the invention utilize, for example, a hydrophobic—hydrophobic interaction between two or more stabilizing moieties to bring the donor and the acceptor into proximity. Recognition of this new mechanism of controlling the conformation of energy transfer probes frees the design of these probes from the restrictions on the sequences of biomolecules used in the probes. Thus, using the present probes, those of skill in the art are able to explore the structure and function of a substantially wider range of species with probes that are easily designed and prepared.

In a first aspect, the present invention provides a CAP probe having a formula selected from:

X—R—A—(Y)$_n$, R—X—A—(Y)$_n$—Q, R—X—A—Q—(Y)$_n$, and X—R—A—(Y)$_n$—Q wherein,

A is a nucleic acid sequence comprising nucleic acid monomers selected from the group consisting of natural nucleic acids, modified nucleic acids and combinations thereof. D is a molecular energy transfer donor. Q is a molecular energy acceptor. X and Y are the same or different and are non-nucleotidic stabilizing moieties that interact to bring R and Q into operative proximity, thereby enabling transfer of energy from R to Q. The subscript n is 0 or 1.

In another aspect, the invention provides a CAP probe having the formula:

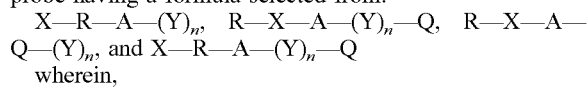

in which, CHOL is a cholesterol derivative. $R^1$, $R^2$, $R^3$ and $R^4$ are linker moieties independently selected from the group consisting of substituted or unsubstituted alkyl and substituted or unsubstituted heteroalkyl. $Nu^1$ and $Nu^2$ are independently selected nucleotide residues and NA is a nucleic acid. D is a donor of light energy and Q is a quencher of light energy.

In a third aspect, the invention provides a CAP probe having the formula:

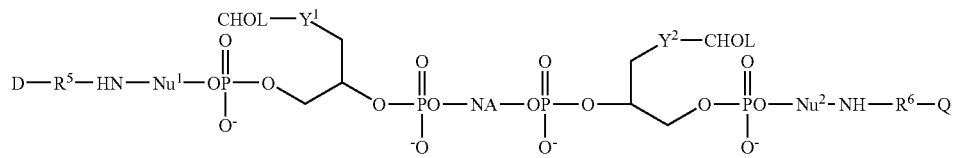

in which, NA is a nucleic acid sequence. $Nu^1$ and $Nu^2$ are independently selected nucleotide residues. $Y^1$ and $Y^2$ are linking groups independently selected from the group consisting of substituted or unsubstituted alkyl and substituted or unsubstituted heteroalkyl. $R^5$ and $R^6$ are linking groups independently selected from the group consisting of substituted or unsubstituted alkyl and substituted or unsubstituted heteroalkyl. D is a donor of light energy and Q is a quencher of light energy.

Design of CAP Probes

The proper selection of stabilizing ligands and energy donor/acceptor pairs is important to the successful design of CAP probes. In choosing stabilizing moieties, any two groups that exhibit an affinity for each other can be used to bring the donor and acceptor into the desired proximity. Presently preferred stabilizing moieties are those that meet four criteria: (1) the binding energy of the stabilizing moieties is preferably less than the hybridization energy between the probe sequence and its target sequence; (2) the stabilizing moieties are preferably not themselves quenchers; (3) the stabilizing moieties preferably do not interfere with hybridization of the probe to its target sequence; and (4) the stabilizing ligand/oligonucleotide conjugate is preferably cost-effective to manufacture and easily purified.

The CAPs and CAP components can be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds are prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809–816; and Heller, *Acc. Chem. Res.* 23: 128 (1990).

The characteristics of presently preferred CAPs, CAP components and method for using the CAPs of the invention are discussed below. This discussion is intended to be illustrative and is not limiting of the scope of the components that can be used to assemble a CAP The Nucleic Acids The present invention provides oligonucleotide probes that are labeled with donor and acceptor moieties (i.e., a "MET pair") and at least one stabilizing moiety. A MET pair can comprise any two species that are capable of detectable energy transfer from the donor to the acceptor. In a presently preferred embodiment, the MET pair transfers fluorescence from a donor to an acceptor molecule, referred to herein as fluorescence energy transfer ("FET").

The oligonucleotides of the invention can comprise natural and/or modified nucleobases, sugars and intermonomer linkages. In a presently preferred embodiment, the oligonucleotides of the invention comprise natural nucleotides between the 3'- and 5'-termini. These termini are derivatized with the donor, the acceptor and, preferably one or more stabilizing moieties.

The oligonucleotides for use in the probes of the invention can be any suitable size, and are preferably in the range of from about 10 to about 100 nucleotides, more preferably from about 10 to about 80 nucleotides and more preferably still, from about 20 to about 40 nucleotides. The precise sequence and length of an oligonucleotide probe of the invention depends in part on the nature of the target polynucleotide to which it binds. The binding location and length may be varied to achieve appropriate annealing and melting properties for a particular embodiment. Guidance for making such design choices can be found in many art recognized references.

Preferably, the 3'-terminal nucleotide of the oligonucleotide probe is blocked or rendered incapable of extension by a nucleic acid polymerase. Such blocking is conveniently carried out by the attachment of a donor or acceptor molecule to the terminal 3'-carbon of the oligonucleotide probe by a linking moiety.

The oligonucleotide can comprise DNA, RNA or chimeric mixtures or derivatives or modified versions thereof. In addition to being labeled with an molecular energy transfer donor (R) and a molecular energy transfer acceptor (O) moiety, the oligonucleotide can be modified at the base moiety, sugar moiety, or phosphate backbone with other groups such as radioactive labels, minor groove binders, intercalating agents an the like.

For example, the oligonucleotide can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

Phosphodiester linked oligonucleotides of the invention can be synthesized by standard methods known in the art, e.g. by use of an automated DNA synthesizer (such as are commercially available from P.E. Biosystems, etc.) using commercially available amidite chemistries. Oligonucleotides bearing modified phosphodiester linking groups can be synthesized by methods known in the art. For example, phosphorothioate oligonucleotides may be synthesized by the method of Stein et al. (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448–7451 (1988)). Other methods of synthesizing both phosphodiester- and modified phosphodiester-linked oligonucleotides will be apparent to those of skill in the art.

Oligonucleotide probes of the invention can be synthesized by a number of approaches, e.g., Ozaki et al., *Nucleic Acids Research,* 20: 5205–5214 (1992); Agrawal et al., *Nucleic Acids Research,* 18: 5419–5423 (1990); or the like. The oligonucleotide probes of the invention are conveniently synthesized on an automated DNA synthesizer, e.g., a P.E. Biosystems, Inc. (Foster City, Calif.) model 392 or 394 DNA/RNA Synthesizer, using standard chemistries, such as phosphoramidite chemistry (see, for example, disclosed in the following references: Beaucage et al., *Tetrahedron,* 48: 2223–2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679). Alternative chemistries resulting in non-natural backbone groups, such as phosphorothioate, phosphoramidate, and the like, may also be employed.

When the oligonucleotides are synthesized utilizing an automated DNA synthesizer, the stabilizing moiety, energy transfer donor and energy transfer acceptor moieties are preferably introduced during automated synthesis. Alternatively, one or more of these moieties can be introduced either before or after the automated synthesis procedure has commenced. In another exemplary embodiment, one or more of these moieties is introduced after the automated synthesis is complete.

In a preferred embodiment, at least one of the stabilizing moieties is a cholesteryl residue. In this embodiment, the cholesteryl residue is preferably introduced using a commercially available cholesteryl amidite (Glen Research). In another preferred embodiment, at least one of the stabilizing moieties is an alkyl group. The alkyl group is preferably introduced using, for example, convertible amidites or alkyl amidites (Biosearch). Additional strategies for attaching stabilizing groups to growing or complete oligonucleotides will be apparent to those of skill in the art.

Once the desired oligonucleotide is synthesized, it is preferably cleaved from the solid support on which it was synthesized and treated, by methods known in the art, to remove any protecting groups present (e.g., 60° C., 5 h, concentrated ammonia). In those embodiments in which a base-sensitive group is attached to the oligonucleotides (e.g., TAMRA), the deprotection will preferably use milder conditions (e.g., butylamine: water 1:3, 8 hours, 70° C.). Deprotection under these conditions is facilitated by the use of quick deprotect amidites (e.g., dC-acetyl, dG-dmf).

Following cleavage from the support and deprotection, the oligonucleotide is purified by any method known in the art, including chromatography, extraction and gel purification. In a preferred embodiment, the oligonucleotide is purified using HPLC. The concentration and purity of the isolated oligonucleotide is preferably determined by measuring the optical density at 260 nm in a spectrophotometer.

Stabilizing Moieties

As used herein, the term "stabilizing moiety" refers to one or more molecules attached to the oligonucleotide probe. The stabilizing moiety interacts with a component of the CAP to induce a transient and reversible conformation of the probe wherein the energy donor and energy acceptor are in close proximity. Components of the probe that can interact with the stabilizing moiety include a second stabilizing moiety of the same or different structure, the oligonucleotide, the energy donor, the energy acceptor or a combination of more than one of these components. The stabilizing moiety can induce the transient conformation using either attractive or repulsive forces. For example, a stabilizing group that repels another component of the CAP can be used to force the donor and acceptor proximate to each other. Exemplary repulsive mechanisms include, but are not limited to, incompatible steric characteristics, charge—charge repulsion, hydrophilic-hydrophobic interactions and the like.

In a preferred embodiment, the transient conformation is induced by an attractive mechanism between the stabilizing moiety and another component of the CAP. Exemplary attractive forces include, ionic bonding, ion pairing, van der Waals association, hydrophobic—hydrophobic interactions, complexation and host-guest mechanisms. In a preferred embodiment, stabilizing agents will interact by a hydrophobic—hydrophobic mechanism and X and Y are both hydrophobic moieties. In a still further preferred embodiment, X and Y are members independently selected from saturated hydrocarbons, unsaturated hydrocarbons, steroids, fatty acids, fatty alcohols and hydrophobic peptides. See, for example, Boutorin et al., *FEBS Lett.*, 254: 129–132 (1989); Gryaznov et al., *Nucleic Acids Research*, 21: 5909–5915 (1993); Kreig et al., *Proc. Natl. Acad. Sci. USA*, 90: 1048–1052 (1993); Letsinger et al., *J. Am. Chem. Soc.*, 115: 7535–7536 (1993); Letsinger et al., *Proc. Natl. Acad. Sci. USA*, 86: 6553–6556 (1989); Hecht, *Biochemistry*, 27: 7237 (1988); Shea et al., *Nucleic Acids Res.*, 18: 3777–3783 (1990).

Stabilizing moieties can also be selected from a wide range of small organic molecules, organic functional groups (e.g., amines, carbonyls, carboxylates, etc.), biomolecules, metals, metal chelates and organometallic compounds.

When the stabilizing moiety is an amine, in preferred embodiments, the stabilizing moiety will interact with a component of the CAP (e.g., carboxyl groups, phosphate groups) that is complementary to (e.g., complexing, ion-pairing) with the amine. In another preferred embodiment, the amine is protonated by an acidic moiety on the CAP (e.g., carboxylic acid, sulfonic acid).

In certain preferred embodiments, when the stabilizing moiety is a carboxylic, or other acid, the stabilizing moiety will interact with a component of the CAP by, for example, complexation (e.g., metal ions) or ion-pairing (e.g., quaternary ammonium cations). In still other preferred embodiments, the carboxylic acid will protonate a basic group on the CAP (e.g. amine).

When the stabilizing moiety is a chelating agent, crown ether or cyclodextrin, host-guest chemistry will preferably dominate the interaction between the stabilizing moiety and the complementary component of the CAP. The use of host-guest chemistry allows a great degree of stabilizing-moiety-complementary CAP component specificity to be engineered into a CAP of the invention. The use of these compounds to bind to specific compounds is well known to those of skill in the art. See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279–312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

In another preferred embodiment, the stabilizing moiety forms an inclusion complex with the complementary CAP component. In a particularly preferred embodiment, the stabilizing moiety is a cyclodextrin or modified cyclodextrin. Cyclodextrins are a group of cyclic oligosaccharides produced by numerous microorganisms. These basket shaped polysaccharides are able to form inclusion complexes with an array of organic molecules including, for example, drugs, pesticides, herbicides and agents of war. See, Tenjarla et al., *J. Pharm. Sci.*, 87: 425–429 (1998); Zughul et al., *Pharm. Dev. Technol.*, 3: 43–53 (1998); and Albers et al., *Crit. Rev. Ther. Drug Carrier Syst.*, 12: 311–337 (1995); Szejtli, CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978.

In another exemplary embodiment, the stabilizing moiety is a polyaminocarboxylate chelating agent such as ethylenediaminetetraacetic acid (EDTA) or diethylenetriaminepentaacetic acid (DTPA). In a preferred embodiment, this stabilizing moiety is attached to an amine-containing component of a CAP or a linker group attached to the CAP, for example, by utilizing a commercially available anhydride (Aldrich Chemical Co., Milwaukee, Wis.). This stabilizing moiety, in preferred embodiments will interact with a coordinatively unsaturated metal ion that is attached to the CAP by means of, for example, a second chelating agent. In an exemplary embodiment, a metal ion-based stabilizing moiety exhibits an affinity for phosphorous containing moieties. Representative groups having this affinity include, but are not limited to, $Cu^{+2}$-diamine, triethylentetraamine-$Cu^+$ 2-chloride, tetraethylenediamine-Cu $^{+2}$-chloride and 2,2'-bipyridine-$Cu^{+2}$-chloride. See, U.S. Pat. No. 4,549,427, issued to Kolesar, Jr., E. S. on Oct. 29, 1985.

In still further preferred embodiments, the stabilizing moiety is a biomolecule such as a protein, nucleic acid, peptide or an antibody. Biomolecules useful in practicing the present invention can be derived from any source. The biomolecules can be isolated from natural sources or they can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Moreover, antibody fragments containing the recognition component can be used, rather than the whole antibody. Peptides and nucleic acids can also be used and these can be isolated from natural sources or they can be wholly or partially synthetic in origin.

In those embodiments wherein the stabilizing moiety is a protein or antibody, the protein can be tethered directly to a CAP component or via a linker group through any reactive peptide residue available on the surface of the protein. In preferred embodiments, the reactive groups are amines or carboxylates. In particularly preferred embodiments, the reactive groups are the $\epsilon$-amine groups of lysine residues.

Stabilizing moieties that are antibodies can be used to recognize numerous CAP components including, proteins, peptides, nucleic acids, saccharides or small molecules such as drugs, herbicides, pesticides and the like. Methods of raising antibodies for specific molecules are well-known to those of skill in the art. See, U.S. Pat. No. 5,147,786, issued to Feng et al. on Sep. 15, 1992; No. 5,334,528, issued to Stanker et al. on Aug. 2, 1994; No. 5,686,237, issued to Al-Bayati, M. A. S. on Nov. 11, 1997; and No. 5,573,922, issued to Hoess et al. on Nov. 12, 1996. Methods for attaching antibodies to other molecules are also known in the art. See, for example, Delamarche et al. *Langmuir,* 12: 1944–1946 (1996), Hermanson, BIOCONJUGATE TECHNIQUES, Academic press, San Diego, 1996.

Donor and Acceptor Moieties

A wide range of energy donor and energy acceptor molecules using a variety of energy transfer mechanisms can be used in practicing the present invention representative donor/acceptor pairs include fluorophore/quencher, radio-isotope/scintillant, nmr sensitive nuclei/unpaired electron and the like.

In a presently preferred embodiment, the donor/acceptor pair comprises a fluorophore and a quencher. See, for example, Cardullo et al., *Proc. Natl. Acad. Sci. USA,* 85: 8790–8794 (1988); Dexter, D. L., *J of Chemical Physics,* 21: 836–850 (1953); Hochstrasser et al., *Biophysical Chemistry,* 45: 133–141 (1992); Selvin, P., *Methods in Enzymology,* 246: 300–334 (1995); Steinberg, I., *Ann. Rev. Biochem.,* 40: 83–114 (1971); Stryer, L., *Ann. Rev. Biochem.,* 47: 819–846 (1978); Wang et al., *Tetrahedron Letters,* 31: 6493–6496 (1990); Wang et al., *Anal. Chem.,* 67: 1197–1203 (1995).

Fluorescent labels have the advantage of requiring few precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Many fluorescent labels are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful in the present invention. Such proteins include, for example, green fluorescent proteins of cnidarians (Ward et al., *Photochem. Photobiol.* 35:803–808 (1982); Levine et al., *Comp. Biochem. Physiol.,* 72B:77–85 (1982)), yellow fluorescent protein from Vibrio fischeri strain (Baldwin et al., *Biochemistry* 29:5509–15 (1990)), Peridinin-chlorophyll from the dinoflagellate Symbiodinium sp. (Morris et al., *Plant Molecular Biology* 24:673:77 (1994)), phycobiliproteins from marine cyanobacteria, such as Synechococcus, e.g., phycoerythrin and phycocyanin (Wilbanks et al., *J. Biol. Chem.* 268:1226–35 (1993)), and the like.

The compounds, probes and methods discussed herein are generally representative of the compositions of the invention and the methods in which such compositions can be used. The following discussion is intended as illustrative of selected aspects and embodiments of the present invention and it should not be interpreted as limiting the scope of the present invention.

A non-limiting list of exemplary donors and acceptors operating on the principle of fluorescence energy transfer (FET) is provided in Table 1.

TABLE 1

Suitable moieties that can be selected as donors or acceptors in FET pairs 4-acetamido-4'-isothiocyanatostilbene-2,2'disulfonic acid
acridine and derivatives:

acridine
acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:

coumarin
7-amino-4-methylcoumarin (AMC, Coumarin 120)
7-amino-4-trifluoromethylcouluarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:

eosin
eosin isothiocyanate
erythrosin and derivatives:

erythrosin B
erythrosin isothiocyanate
ethidium
fluorescein and derivatives:

5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
fluorescein
fluorescein isothiocyanate
QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:

pyrene
pyrene butyrate
succinimidyl 1-pyrene butyrate
quantum dots
Reactive Red 4 (Cibacron ™ Brilliant Red 3B-A)
rhodamine and derivatives:

6-carboxy-X-rhodamine (ROX)
6-carboxyrhodamine (R6G)
lissamine rhodamine B sulfonyl chloride rhodamine (Rhod)
rhodamine B

TABLE 1-continued

Suitable moieties that can be selected
as donors or acceptors in FET pairs rhodamine 123
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA)
tetramethyl rhodamine
tetramethyl rhodamine isothiocyanate (TRITC)
riboflavin
rosolic acid
terbium chelate derivatives There is a great deal of practical guidance available in the literature for selecting appropriate donor-acceptor pairs for particular probes, as exemplified by the following references: Pesce et al., Eds., Fluorescence Spectroscopy (Marcel Dekker, New York, 1971); White et al., Fluorescence Analysis: A Practical Approach (Marcel Dekker, New York, 1970); and the like. The literature also includes references providing exhaustive lists of fluorescent and chromogenic molecules and their relevant optical properties for choosing reporter-quencher pairs (see, for example, Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, Ed., Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like. Further, there is extensive guidance in the literature for derivatizing reporter and quencher molecules for covalent attachment via common reactive groups that can be added to an oligonucleotide, as exemplified by the following references: Haugland (supra); Ullman et al., U.S. Pat. No. 3,996,345; Khanna et al., U.S. Pat. No. 4,351,760.

Preferably, donor molecules are fluorescent organic dyes derivatized for attachment to the terminal 3'-carbon or terminal 5'-carbon of the probe via a linking moiety. Preferably, acceptor molecules are also organic dyes, which may or may not be fluorescent, depending on the embodiment of the invention. For example, in a preferred embodiment of the invention, the acceptor molecule is fluorescent. Generally whether the acceptor molecule is fluorescent or simply releases the transferred energy from the reporter by non-radiative decay, the absorption band of the acceptor should substantially overlap the fluorescent emission band of the donor. Non-fluorescent acceptor molecules that absorb energy from excited donor molecules, but which do not release the energy radiatively, are referred to as "dark quenchers." Presently preferred dark quenchers are the "Black Hole quenchers" described in the commonly owned copending U.S. patent application Ser. No. 09/567,863, entitled "Dark Quenchers for Donor Acceptor Energy Transfer," filed on May 9, 2000, the disclosure of which is incorporated herein by reference.

In a further embodiment of the present invention, the acceptor moiety is a fluorophore that releases energy that it absorbs from the donor at a different wavelength; use of the emissions of the donor and/or acceptor may then be measured to assess the progress of the amplification reaction, depending on whether the donor and acceptor moieties are incorporated into the amplification product close enough for MET to occur. In another embodiment, the acceptor moiety is a quencher that quenches the fluorescence of the donor when the donor and acceptor moieties are incorporated into the amplification product close enough for MET to occur.

In a further specific embodiment, an oligonucleotide primer is used that forms a hairpin structure in which FET will occur when the primer is in the hairpin configuration. In a preferred embodiment, the hairpin probe is labeled with a donor-quencher FET pair. When the configuration of the hairpin probe changes to a substantially open-chain configuration (e.g., when it is incorporated into an amplification product), quenching is eliminated or reduced, and the fluorescence of the donor can be detected. In presently preferred probes of this design, the fluorescence intensity of the probe hybridized to the target polynucleotide is preferably at least about a factor of 6 greater than the fluorescence intensity of the probe when not hybridized to the target polynucleotide.

The donor moiety is preferably separated from the acceptor moiety by at least about 10 nucleotides, and more preferably by at least about 15 nucleotides. The donor moiety is preferably attached to either the 3'- or 5'-terminal nucleotides of the probe. The acceptor moiety is also preferably attached to either the 3'- or 5'-terminal nucleotides of the probe. More preferably, the donor and acceptor moieties are attached to the 3'- and 5'- or 5'- and 3'-terminal nucleotides of the probe, respectively.

Exemplary donor-acceptor pairs are selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

In a presently preferred embodiment, the reporter molecule is a fluorescein dye and the quencher molecule is preferably a rhodamine dye. The fluorescein moiety is preferably attached to the 5'-terminus of the oligonucleotide. This donor is preferably introduced using the 6-FAM amidite. In other embodiments, utilizing different donor groups, these groups are preferably introduced using an amidite derivative of the reporter group. Alternatively, reporter groups comprising reactive groups (e.g., isothiocyanates, active esters, etc.) can be introduced via reaction with a reactive moiety on a tether or linker arm attached to the oligonucleotide (e.g., hexyl amine).

In yet another preferred embodiment, the acceptor moiety is derived from TAMRA (tetramethylrhodamine carboxylic acid). This acceptor is preferably attached using a solid support that is derivatized with the acceptor (Biosearch Technologies, Inc.)

In view of the well-developed body of literature concerning the conjugation of small molecules to oligonucleotides, many other methods of attaching donor/acceptor pairs to oligonucleotides will be apparent to those of skill in the art. For example, rhodamine and fluorescein dyes are also conveniently attached to the 5'-hydroxyl of an oligonucleotide at the conclusion of solid phase synthesis by way of dyes derivatized with a phosphoramidite moiety (see, for example, Woo et al., U.S. Pat. No. 5,231,191; and Hobbs, Jr., U.S. Pat. No. 4,997,928).

Linker Groups

As used herein, the term "linker group," refers to constituents of CAPs that link stabilizing moieties, donor and/or acceptor moieties and other groups to the oligonucleotide component of the CAP. The linker groups can be hydrophilic (e.g., polyethylene glycol) or they can be hydrophobic (e.g., hexane, decane, etc.)

In certain embodiments, it is advantageous to have a stabilizing moiety or other component of the CAP attached to the oligonucleotide component by a group that provides flexibility and distance from the oligonucleotide. In this embodiment, the group to which the stabilizing moiety is bound is referred to as a "linker group" or "spacer." Using such linker groups, the properties of the oligonucleotide adjacent to the stabilizing moiety can be modulated. Properties that are usefully controlled include, for example, hydrophobicity, hydrophilicity, surface-activity and the distance of the stabilizing moiety from the oligonucleotide.

In an exemplary embodiment, the spacer serves to distance the reactive group and/or stabilizing moiety from the oligonucleotide. Spacers with this characteristic have several uses. For example, a stabilizing moiety held too closely to the oligonucleotide may not interact with its complementary group, or it may interact with too low of an affinity. When a stabilizing moiety is itself sterically demanding, the reaction leading to stabilizing moiety-complementary group interaction can be undesirably weakened, or it may not occur at all, due to a sterically-induced hindering of the approach of the two components.

In yet a further embodiment, the linker group is provided with a group that can be cleaved to release a stabilizing moiety, minor groove binder, intercalating moiety and/or acceptor moiety from the oligonucleotide. Many cleaveable groups are known in the art. See, for example, Jung et al., *Biochem. Biophys. Acta*, 761: 152–162 (1983); Joshi et al., *J. Biol. Chem.*, 265: 14518–14525 (1990); Zarling et al., *J. Immunol.*, 124: 913–920 (1980); Bouizar et al., *Eur. J. Biochem.*, 155: 141–147 (1986); Park et al., *J. Biol. Chem.*, 261: 205–210 (1986); Browning et al., *J. Immunol.*, 143: 1859–1867 (1989). Moreover a broad range of cleavable, bifunctional (both homo- and hetero-bifunctional) linker groups are commercially available from suppliers such as Pierce.

Exemplary cleaveable moieties can be cleaved using light, heat or reagents such as thiols, hydroxylamine, bases, periodate and the like. Preferred cleaveable groups comprise a cleaveable moiety which is a member selected from the group consisting of disulfide, ester, imide, carbonate, nitrobenzyl, phenacyl and benzoin groups.

Hybridization Enhancers

In another embodiment, the CAPs of the invention comprise a moiety that enhances the hybridization between the CAP and its complementary strand. In a presently preferred embodiment, the hybridization enhancing moiety is a member selected from the group consisting of intercalating agents (e.g., polycyclic aromatic hydrocarbons, see, for example, Mann, et al., *Bioconjugate Chem.*, 3(6):554–8 (1992)) Sun, et al., *Proc Natl Acad Sci USA* 86(23):9198–202 (1989) and minor groove binders (MGB), more preferably minor groove binders.

Minor groove binders are crescent shaped antibiotics based on netropsin and distamycin which are known to fit in the minor groove of the double helix leading to stabilization of the duplex. Affinity of the MGB is especially strong for T/A base pairs.

Oligonucleotides conjugated at the terminus with MGBs are known to have significantly higher $T_m$'s than control oligos in the presence of complement. For example, Epoch Pharmaceutical (Seattle, Wash.) has applied this property for the design of high affinity PCR primers and more recently to the design of "Taqman-MGB" probes (Meyer, R., "Oligonucleotide-Minor Groove Binder Conjugates as Probes and Primers", presented at CHI Symposium, SF, CA, Jun. 24–25, 1998).

The Taqman-MGB probe overcomes problems associated with traditional Taqman probes: because MGB probes have high Tm's they may be used to interrogate A/T rich sequences, whereas a Taqman probe of reasonable length (<35-mer) would not bind at such regions under the assay condition (65° C.).

Conjugation

The above enumerated stabilizing, energy donor, energy acceptor, minor groove binding, intercalating and other molecules, can be attached to the oligonucleotide by methods well-known to those of skill in the art. Ample guidance can be found in literature devoted to, for example, the fields of bioconjugate chemistry and drug delivery. For example, one of skill, presented with a stabilizing or other moiety comprising an available amine will be able to choose from among a variety of amine derivatizing reactions, locate an appropriately functionalized partner (e.g., a carboxylic acid terminated moiety) for the oligonucleotide and react the partners under conditions chosen to effect the desired coupling (e.g., dehydrating agents, e.g., dicyclohexylcarbodiimide). See, for example, MODIFICATION OF PROTEINS: FOOD, NUTRITIONAL, AND PHARMACOLOGICAL ASPECTS, Feeney et al., Eds., American Chemical Society, Washington, D.C., 1982, pp. 370–387; POLYMERIC DRUGS AND DRUG DELIVERY SYSTEMS, Dunn et al., Eds., American Chemical Society, Washington, D.C., 1991.

In general, the components of the probes of the invention are linked together through the use of reactive groups, which are typically transformed by the linking process into a new organic functional group. The reactive functional group(s), is located at any position on an aryl nucleus or on a chain, such as an alkyl chain, attached to an aryl nucleus. When the reactive group is attached to an alkyl, or substituted alkyl chain, the reactive group is preferably located at a terminal position of an alkyl chain. Reactive groups and classes of reactions useful in practicing the present invention are generally those that are well known in the art of bioconjugate chemistry. Currently favored classes of reactions available with reactive Group are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon—carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble the Probe Component. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

The discussion that follows focuses on the attachment of a reactive stabilizing moiety to an assembled reactive oligonucleotide of a CAP. This focus is for convenience only and one of skill in the art will understand that the discussion is equally applicable to embodiments in which the CAP component (e.g., donor, acceptor, minor groove binder) and the stabilizing moiety are preformed into a "cassette" that is subsequently attached to the reactive oligonucleotide. This discussion is similarly applicable to donor and/or acceptor moieties, minor groove binders, intercalating agents and the like. As used herein, "reactive stabilizing agents" refers to stabilizing components that have a functional group available for reaction with an oligonucleotide, for example, or other species following the assembly of the oligonucleotide. Reactive groups which can be used in practicing the present invention include, for example, amines, hydroxyl groups, carboxylic acids, carboxylic acid derivatives, alkenes, sulfhydryls, etc.

More specifically, there are many linking moieties and methodologies for attaching groups to the 5'- or 3'-termini of oligonucleotides, as exemplified by the following references: Eckstein, editor, Oligonucleotides and Analogues: A Practical Approach (IRL Press, Oxford, 1991); Zuckerman et al., Nucleic Acids Research, 15: 5305–5321 (1987) (3'-thiol group on oligonucleotide); Sharma et al., Nucleic Acids Research, 19: 3019 (1991) (3'-sulfhydryl); Giusti et al., PCR Methods and Applications, 2: 223–227 (1993) and Fung et al., U.S. Pat. No. 4,757,141 (5'-phosphoamino group via Aminolink TM II available from P.E. Biosystems, CA.) Stabinsky, U.S. Pat. No. 4,739,044 (3-aminoalkylphosphoryl group); Agrawal et al., Tetrahedron Letters, 31: 1543–1546 (1990) (attachment via phosphoramidate linkages); Sproat et al., Nucleic Acids Research, 15: 4837 (1987) (5-mercapto group); Nelson et al., Nucleic Acids Research, 17: 7187–7194 (1989) (3'-amino group), and the like.

As discussed above a stabilizing moiety (or other CAP component) can be conjugated to an oligonucleotide by any of a large number of art-known attachment methods and strategies. For example, in one preferred embodiment, a reactive linker group is attached to the oligonucleotide and the stabilizing moiety is subsequently bound to the linker group via reaction between a reactive group on the spacer and a group of complementary reactivity on the stabilizing moiety. See, for example, Hegner et al., Biophys. J., 70: 2052–2066 (1996).

In another preferred embodiment, the stabilizing moiety is attached to a subunit of the oligonucleotide prior to beginning the synthesis of the oligonucleotide. Nucleic acids can be derivatized through a reactive group on a base (e.g., exocyclic amine) or an available hydroxyl group on a sugar moiety (e.g., 3'- or 5'-hydroxyl). The nucleic acid chains can be further derivatized at one or more sites to allow for the attachment of appropriate reactive groups onto the chain. See, Chrisey et al., Nucleic Acids Res., 24: 3031–3039 (1996). In a preferred embodiment, the stabilizing moiety is attached to the solid support on which the synthesis occurs and is tethered to the 3'-hydroxy terminus of the oligonucleotide.

In addition to small molecule stabilizing agents, peptide-based stabilizing or targeting moieties can also be attached to the oligonucleotide component. Both naturally-derived and synthetic peptides are of use in conjunction with the present invention. These molecules can be attached to an oligonucleotide or other CAP component by any available reactive group including, for example, amine, carboxyl, sulfhydryl and hydroxyl groups. Such groups can reside at a peptide terminus or at a site internal to the peptide chain.

When the peptide is a fully or partially synthetic molecule, a reactive group or masked reactive group can be incorporated during the process of the synthesis. Many derivatized monomers appropriate for reactive group incorporation into peptides are know to those of skill in the art. See, for example, "Special Methods in Peptide Synthesis," In, THE PEPTIDES: ANALYSIS, SYNTHESIS, BIOLOGY, Vol. 2: Gross, et al., Eds., Academic Press, New York (1980). Many useful monomers are commercially available (Bachem, Sigma, etc.). When the amino acid monomer contains a masked reactive group, this group can be unmasked following the synthesis, at which time it becomes available for reaction with an oligonucleotide component, a linker group or can be incorporated into a cassette with, for example, a donor or acceptor moiety.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370–387; Kasina et al., Bioconjugate Chem., 9: 108–117 (1998); Song et al., Bioconjugate Chem., 8: 249–255 (1997).

Cyclodextrin-based stabilizing moieties are preferably attached to a CAP component, through a linker group. See, Yamamoto et al., *J. Phys. Chem. B*, 101: 6855–6860 (1997). Methods to attach cyclodextrins to other molecules are well known to those of skill in the chromatographic and pharmaceutical arts. See, Sreenivasan, K. J., *Appl. Polym. Sci.*, 60: 2245–2249 (1996).

Changes of State

The CAPs of the present invention can be assembled such that one or more CAP components comprises a switchable group that undergoes a change of state upon being contacted by some external agent or force. For example, the switchable group can be a component of the stabilizing moiety or, if a linker group is used to attach the stabilizing moiety to the oligonucleotide, the switchable group can form a component of the linker group. The change in state can be, for example, an alteration in the conformation, electronic configuration, charge, polarity, dipole moment or steric bulk of the group. The change in state of the group can be utilized to affect CAP properties and to assemble CAPs that are switchable between at least two different states.

The change in state can be brought about by a range of external conditions or forces including, for example, changes in fluid pH, ionic strength and/or redox potential. Additionally, changes in state can be brought about by exposing the switchable group to forces such as light, heat, magnetic and electrical fields.

In a preferred embodiment, the change of state is utilized to alter the availability of a stabilizing moiety to its binding partner (e.g., a second stabilizing moiety). For example, in a first state, the switchable group can present a stabilizing moiety in a mode in which it interacts with its complementary group. When switched into its second state, the stabilizing moiety becomes unavailable for interaction or it interacts with less affinity. Thus, by switching between the two states a stabilizing moiety can, for example, interact with and then be forced away from its binding partner. Alternatively, the stabilizing moiety can be maintained in its non-interacting conformation until a desired time when the change of state is initiated and the stabilizing moiety interacts with its complementary group.

In another preferred embodiment, the switchable group can be used to vary the size or the charge of the stabilizing group and/or linker group. For example, a group that is switched by a change in pH might exist in both an acidic and a basic form. In one example, the acidic form will be charged (e.g., amine to ammonium cation).

Switchable groups appropriate for use in conjunction with the present invention include, for example, azobenzene derivatives. Azobenzenes exist in one of two switchable isomers, the "trans" and the "cis" isomers. See, for example, Yu et al., *Langmuir* 12: 2843–2848 (1996); Kumano et al., *Polymer J.* 16(6): 461–470 (1984); Seki et al., *Langmuir* 9: 211–217 (1993); and Sekkat et al., *Langmuir* 11: 2855–2859 (1995). Other useful groups include, for example, spiropyrans and related compounds and redox couples such as ferrocene (Chidsey, *Science* 251: 919 (1991)), viologen (DeLong et al., *Langmuir* 6: 709 (1992)), and ruthenium polypyridyl complexes (Finkles et al., *J. Am. Chem. Soc.* 114: 3173 (1992)). Other useful switchable groups will be apparent to those of skill in the art.

Molecular Beacon-like CAPs

In another preferred embodiment, the present invention provides CAP probes that are analogous to art-recognized molecular beacons. CAPs are, however, distinguishable from molecular beacons, because CAPs rely on non-nucleotidic stabilizng moieties. In concept, CAP probes can be regarded as "affinity beacons". As discussed above, CAPs use intramolecular attractive forces to favor conformations resulting in donor/acceptor interaction, while beacons take advantage of hydrogen bonding of complimentary nucleic acid bases. The simplicity of design and improved economics of manufacture of CAPs have decided advantages over beacons.

Figure 6:
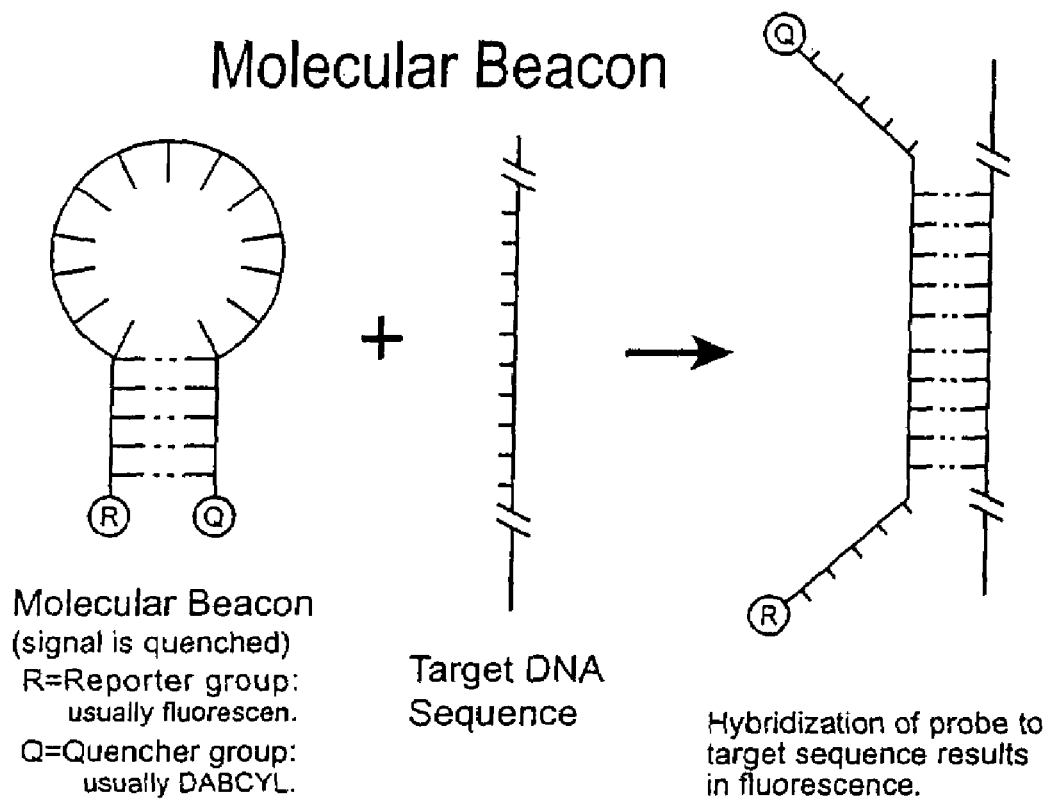
FIG. 6 is a schematic diagram of a molecular beacon and its hybridization to a target nucleic acid.
Figure 7:
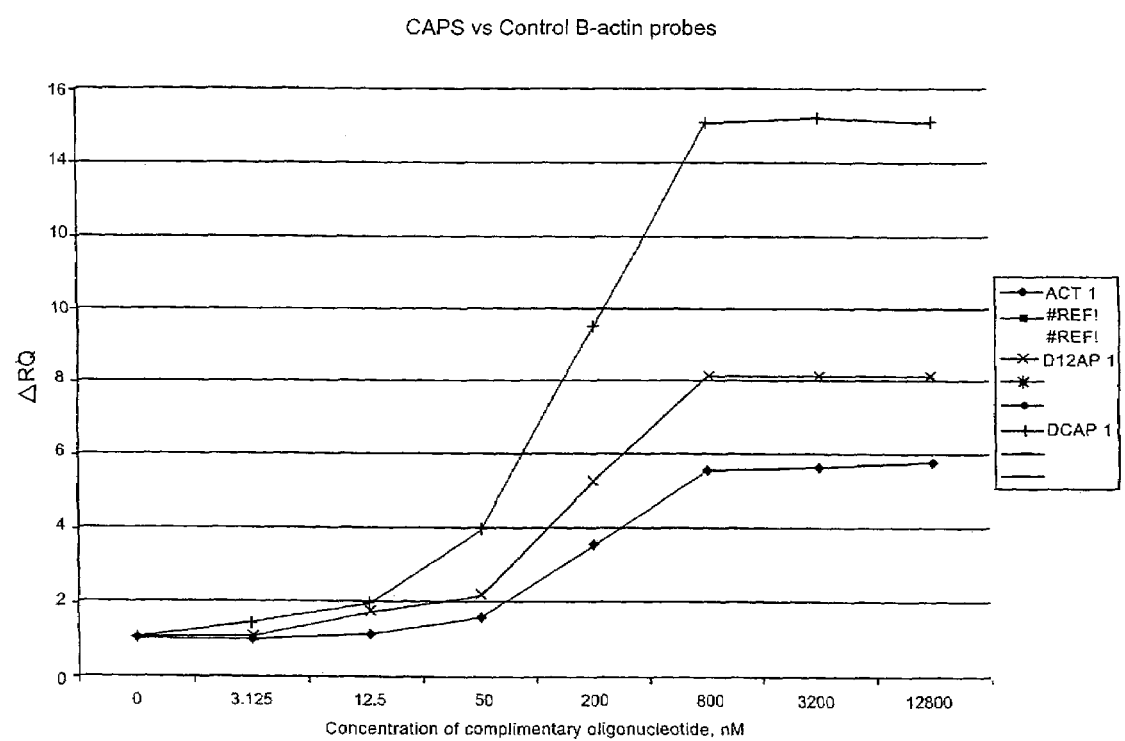
FIG. 7 is a graphic display of ΔRQ vs. concentration of complementary oligonucleotide for CAPs and a control B-actin probe: (X) D12AP; (+) DCAP; (♦) ACT1.

Molecular beacons are self quenched fluorescent oligonucleotide probes that detect the presence of specific nucleic acids. They are useful in situations where it is either not possible or desirable to isolate the probe-target hybrids from an excess of the hybridization probes, such as in real time monitoring of polymerase chain reactions in sealed tubes or in detection of RNAs within living cells. To solve the problem of poor quenching by separated fluorophore/quencher, a class of self quenching probes know as molecular beacons have been recently introduced. Molecular beacons are designed as a two component stem-loop hybrid system: the loop structure is a probe sequence complementary to a genetic target, while the self-complimentary stem is with a fluorophore and quencher placed at the adjacent termini (FIG. 6). Typically, the stem consists of about 5–8 bases and is GC rich. The loop may be designed as a 15–30-mer probe with annealing temperature of about 60° C. The duplex stem maintains the fluorophore/quencher in close proximity to each other, leading to effective quenching. The quencher commonly specified for beacons is DABCYL, a non-fluorescent azo dye chromophore, that emits the absorbed energy as heat. When the probe encounters a target molecule, it forms a duplex that is longer and more stable than the stem, resulting in disassociation of the fluorophore/quencher and consequent fluorophore signaling.

Solid Support Immobilized CAPs

Figure 4:
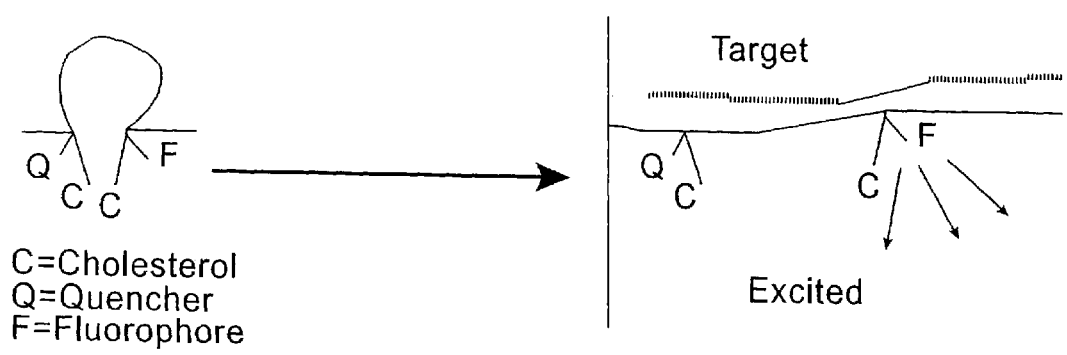
FIG. 4 is a schematic diagram of an immobilized CAP probe capturing a solution-phase target nucleic acid.

In one embodiment, the CAP of the present invention is immobilized on a solid support. In a preferred embodiment, the immobilized CAP is used as a capture probe (FIG. 4).

The oligonucleotide probe can be attached directly to the solid support, for example by attachment of the 3'- or 5'-terminal nucleotide of the probe to the solid support. More preferably, however, the probe is attached to the solid support by a linker (i.e., linker group, supra). The linker serves to distance the probe from the solid support. The linker is most preferably from about 5 to about 30 atoms in length, more preferably from about 10 to about 50 atoms in length.

Examples of preferred types of solid supports for immobilization of the oligonucleotide probe include controlled pore glass, glass plates, polystyrene, avidin coated polystyrene beads, cellulose, nylon, acrylamide gel and activated dextran. CPG, glass plates and high cross-linked polystyrene. These solid supports are preferred for hybridization and diagnostic studies because of their chemical stability, ease of functionalization and well defined surface area. Solid supports such as controlled pore glass (CPG, 500 Å, 1000 Å) and non-swelling high cross-linked polystyrene (1000 Å) are particularly preferred in view of their compatibility with oligonucleotide synthesis.

The oligonucleotide probe may be attached to the solid support in a variety of manners. For example, the probe may be attached to the solid support by attachment of the 3'- or 5'-terminal nucleotide of the probe to the solid support. In other embodiments, the probe is attached to the solid support through a nucleotide located between the 3'- and 5'-termini.

In yet another preferred embodiment, the solid support is also used as the synthesis support in preparing the CAP. The length and chemical stability of the linker between the solid support and the first 3'-unit of oligonucleotides play an important role in efficient synthesis and hybridization of support bound oligonucleotides. The linker arm should be sufficiently long so that a high yield (>97%) can be achieved during automated synthesis. The required length of the linker will depend on the particular solid support used. For example, a six atom linker is generally sufficient to achieve a >97% yield during automated synthesis of oligonucleotides when high cross-linked polystyrene is used as the solid support. The linker arm is preferably at least 20 atoms long in order to attain a high yield (>97%) during automated synthesis when CPG is used as the solid support.

Hybridization of a probe immobilized to a solid support generally requires that the probe be separated from the solid support by at least 30 atoms, more preferably at least 50 atoms. In order to achieve this separation, the linker generally includes a spacer positioned between the linker and the 3'-terminus. For oligonucleotide synthesis, the linker arm is usually attached to the 3'-OH of the 3'-terminus by an ester linkage which can be cleaved with basic reagents to free the oligonucleotide from the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. Such polymers are preferred over homopolymeric oligonucleotides because they do not significantly interfere with the hybridization of probe to the target oligonucleotide. Polyethylene glycol is particularly preferred because it is commercially available, soluble in both organic and aqueous media, easy to functionalize, and completely stable under oligonucleotide synthesis and post-synthesis conditions.

The linkages between the solid support, the linker and the probe are preferably not cleaved during removal of base protecting groups under basic conditions at high temperature. These linkages can, however, be selected from groups that are cleavable under a variety of conditions. Examples of presently preferred linkages include carbamate and amide linkages.

Acrylamide-Immobilized CAPs

In another preferred embodiment, CAP probes are immobilized within a matrix, such as an acrylamide matrix. In a preferred embodiment, the immobilization is accomplished in conjunction with the "acrydite" process invented and commercialized by Mosaic Technologies (Cambridge, Mass., see, Rehman et al., *Nucleic Acids Research*, 27: 649–655 (1999)). The acrydite method allows immobilization of alkene labeled capture probes within a polymerized polyacrylamide network. When target mixes are run past the immobilized probe band under electrophoresis conditions, the target DNA is captured quantitatively. However, detection of this event currently requires a second probe. By using fluorogenic CAP probes as capture probes, signals could be detected directly in real time. A presently preferred format for this embodiment is a CAP probe having the structure, Alkene-Linker-5-FAM-CHOL-Probe-CHOL-Acceptor-3'.

Nucleic Acid Microarrays

DNA microarrays consisting of a multitude of immobilized oligonucleotides have become revolutionary tools for the generation of genomic information, see, Debouck et al., in supplement to *Nature Genetics*, 21:48–50 (1999).

Thus, in another preferred embodiment, the compounds of the present invention are utilized in a microarray format. The CAPs can themselves be components of a microarray or, alternatively they can be utilized as a tool to screen components of a microarray.

In a presently preferred embodiment, the array comprises immobilized fluorogenic CAP probes as the interrogating species. In this embodiment, the CAP probe "turns on" when hybridized to its target. Such arrays are easily prepared and read, and can be designed to give quantitative data. Arrays comprising n CAP probes are valuable tools for expression analysis and clinical genomic screening.

The microarrays can comprise n CAPs that comprise identical or different oligonucleotide sequences. Alternatively, the microarray can comprise a mixture of CAPS comprising groups of identical and different oligonucleotide sequences (e.g., n–m (m<n) identical oligonucleotide sequences). In a preferred embodiment, n is a number from 2 to 100, more preferably, from 10 to 1,000, and more preferably from 100 to 10,000. In a still further preferred embodiment, the n CAPs are patterned on a substrate in a manner that allows the identity of each of the n locations to be ascertained.

In yet another preferred embodiment, the invention also provides a method for preparing a microarray of n CAPs comprising, attaching n CAPs to n regions of a substrate. A variety of methods are currently available for making arrays of biological macromolecules, such as arrays nucleic acid molecules. The following discussion focuses on the assembly of a microarray of CAPs, this focus is for reasons of brevity and is intended to be illustrative and not limiting.

One method for making ordered arrays of CAPs on a substrate is a "dot blot" approach. In this method, a vacuum manifold transfers a plurality, e.g., 96, aqueous samples of CAPs from 3 millimeter diameter wells to a substrate. A common variant of this procedure is a "slot-blot" method in which the wells have highly-elongated oval shapes.

The CAP is immobilized on the porous membrane by baking the membrane or exposing it to UV radiation. This is a manual procedure practical for making one array at a time and usually limited to 96 samples per array. "Dot-blot" procedures are therefore generally inadequate for applications in which many thousand samples must be determined.

A more efficient technique employed for making ordered arrays of CAPs uses an array of pins dipped into the wells, e.g., the 96 wells of a microtiter plate, for transferring an array of samples to a substrate, such as a porous membrane. One array includes pins that are designed to spot a membrane in a staggered fashion, for creating an array of 9216 spots in a 22×22 cm area. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39–81 (1990). A limitation of this approach is that the volume of CAP spotted in each pixel of each array is highly variable. In addition, the number of arrays that can be made with each dipping is usually quite small.

An alternate method of creating ordered arrays of CAPs is analogous to that described by Pirrung et al. (U.S. Pat. No. 5,143,854, issued 1992), and also by Fodor et al., (*Science*, 251: 767–773 (1991)). This method involves synthesizing different CAPs at different discrete regions of a particle or other substrate. This method is preferably used with relatively short CAP molecules, e.g., less than 20 bases. A related method has been described by Southern et al. (*Genomics*, 13: 1008–1017 (1992)).

Khrapko, et al., *DNA Sequence*, 1: 375–388 (1991) describes a method of making an oligonucleotide matrix by spotting DNA onto a thin layer of polyacrylamide. The spotting is done manually with a micropipette.

The substrate can also be patterned using techniques such as photolithography (Kleinfield et al., *J. Neurosci.* 8:4098–120 (1998)), photoetching, chemical etching and microcontact printing (Kumar et al., *Langmuir* 10:1498–511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm have been layered onto a substrate. See, Xia, Y.; Whitesides, G., *J. Am. Chem. Soc.* 117:3274–75 (1995). Similarly, using photolithography, patterns with features as small as 1 μm have been produced. See, Hickman et al., *J Vac. Sci. Technol.* 12:607–16 (1994). Patterns which are useful in the present invention include those which comprise features such as wells, enclosures, partitions, recesses, inlets, outlets, channels, troughs, diffraction gratings and the like.

In a presently preferred embodiment, the patterning is used to produce a substrate having a plurality of adjacent wells, indentations or holes to contain the CAPs. In general, each of these substrate features is isolated from the other wells by a raised wall or partition and the wells do not fluidically communicate. Thus, a particle, or other substance, placed in a particular well remains substantially confined to that well. In another preferred embodiment, the patterning allows the creation of channels through the device whereby an analyte or other substance can enter and/or exit the device.

In another embodiment, the CAPs are immobilized by "printing" them directly onto a substrate or, alternatively, a "lift off" technique can be utilized. In the lift off technique, a patterned resist is laid onto the substrate, an organic layer is laid down in those areas not covered by the resist and the resist is subsequently removed. Resists appropriate for use with the substrates of the present invention are known to those of skill in the art. See, for example, Kleinfield et al., *J. Neurosci.* 8:4098–120 (1998). Following removal of the photoresist, a second CAP, having a structure different from the first CAP can be bonded to the substrate on those areas initially covered by the resist. Using this technique, substrates with patterns of CAPs having different characteristics can be produced. Similar substrate configurations are accessible through microprinting a layer with the desired characteristics directly onto the substrate. See, Mrkish, M.; Whitesides, G. M., *Ann. Rev. Biophys. Biomol. Struct.* 25:55–78 (1996).

Purification and Characterization of CAP Probes

Once the synthesis and deprotection of a particular CAP probe is complete, any art-recognized method or combination of methods can be used to purify and characterize the probes of the invention. Presently preferred purification methods include, for example, High Performance Liquid Chromatography (HPLC) and electrophoresis. Presently preferred purification strategies use reverse-phase HPLC.

Following a purification cycle, the purity of the resulting compound is preferably assessed using analytical HPLC in conjunction with UV and/or fluorescence detection. Alternatively, the purity of the probe can be assessed utilizing analytical electrophoresis.

Fluorescence measurements are preferably carried out using solution(s) of the probe and an analytical fluorescence spectrometer. In an exemplary embodiment, the probes are dissolved in a buffer solution (e.g., standard PCR buffer) at a concentration of approximately 100 nM. When the donor is fluorescein, it will be excited at approximately 485 nm. When the acceptor is TAMRA, the emission will be measured at approximately 582 nm. In another embodiment, in which electrophoresis is used, a fluorescence microplate reader can be utilized.

Uses of CAP Probes

Probes

The invention provides CAP probes including including, for example, a target species (e.g., receptor, enzyme, etc.) a ligand for a target species (e.g., nucleic acid, peptide, etc.), a small molecule (e.g., drug, pesticide, etc.), and the like. The probes can be used for in vitro and in vivo applications.

A particularly unexpected and surprising advantage of the CAPs is the quenching of the excited state energy from the fluorophores of the CAPs by the quenchers without the need to design secondary structure forming components (e.g., hairpins, loops, etc.) into, for example, a nucleic acid or peptide to bring the fluorophore and the acceptor into proximity. The energy transfer pairs of probes presently used in the art typically require the introduction of some form of secondary structure in order to function properly, thereby seriously constraining the identity of species that can be used as carrier molecules. Thus, the probes of the present invention can be of simple design, can be produced more inexpensively and used to probe a much greater array of systems in much less time than current art-recognized probes.

The CAPs described herein can be used in a number of methods for genetic analysis. The following discussion offers a non-limiting overview of methods in which the CAPs of the invention find use. It will be apparent to those of skill in the art that the probes of the invention will find use in additional methods now known or later discovered.

The CAPs of the invention are useful in conjunction with nucleic-acid probes and they can be used as detection agents in a variety of DNA amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the CAPs can be used in probes of substantially any format, including, for example, format selected from molecular beacons, Scorpion probes™, Sunrise probes™, light up probes, Invader Detection probes, and TaqMan™ probes. See, for example, Cardullo, R., et al., *Proc. Natl. Acad. Sci. USA*, 85:8790–8794 (1988); Dexter, D. L., *J. Chem. Physics*, 21:836–850 (1953); Hochstrasser, R. A., et al., *Biophysical Chemistry*, 45:133–141 (1992); Selvin, P., *Methods in Enzymology*, 246:300–334 (1995); Steinberg, I., *Ann. Rev. Biochem.*, 40:83–114 (1971); Stryer, L., *Ann. Rev. Biochem.*, 47:819–846 (1978); Wang, G., et al., *Tetrahedron Letters*, 31:6493–6496 (1990); Wang, Y., et al., *Anal. Chem.*, 67:1197–1203 (1995); Debouck, C., et al., in supplement to *nature genetics*, 21:48–50 (1999); Rehman, F. N., et al., *Nucleic Acids Research*, 27:649–655 (1999); Cooper, J. P., et al., *Biochemistry*, 29:9261–9268 (1990); Gibson, E. M., et al., *Genome Methods*, 6:995–1001 (1996); Hochstrasser, R. A., et al., *Biophysical Chemistry*, 45:133–141 (1992); Holland, P. M., et al., *Proc Natl. Acad. Sci USA*, 88:7276–7289 (1991); Lee, L. G., et al., *Nucleic Acids Rsch.*, 21:3761–3766 (1993); Livak, K. J., et al., *PCR Methods and Applications*, Cold Spring Harbor Press (1995); Vamosi, G., et al., *Biophysical Journal*, 71:972–994 (1996); Wittwer, C. T., et al., *Biotechniques*, 22:176–181 (1997); Wittwer, C. T., et al., *Biotechniques*, 22:130–38 (1997); Giesendorf, B. A. J., et al., *Clinical Chemistry*, 44:482–486 (1998); Kostrikis, L. G., et al., *Science*, 279:1228–1229 (1998); Matsuo, T., *Biochemica et Biophysica Acta*, 1379:178–184 (1998); Piatek, A. S., et al., *Nature Biotechnology*, 16:359–363 (1998); Schofield, P., et al., *Appl. Environ. Microbiology*, 63:1143–1147 (1997); Tyagi S., et al., *Nature Biotechnology*, 16:49–53 (1998); Tyagi, S., et al., *Nature Biotechnology*, 14:303–308 (1996); Nazarenko, I. A., et al., *Nucleic Acids Research*, 25:2516–2521 (1997); Uehara, H., et al., *Biotech-* niques, 26:552–558 (1999); D. Whitcombe, et al., *Nature Biotechnology*, 17:804–807 (1999); Lyamichev, V., et al., *Nature Biotechnology*, 17:292 (1999); Daubendiek, et al., *Nature Biotechnology*, 15:273–277 (1997); Lizardi, P. M., et al., *Nature Genetics*, 19:225–232 (1998); Walker, G., et al., *Nucleic Acids Res.*, 20:1691–1696 (1992); Walker, G. T., et al., *Clinical Chemistry*, 42:9–13 (1996); and Compton, J., *Nature*, 350:91–92 (1991).

The CAPs of the present invention can be used as hybridization probes to detect target polynucleotides. Accordingly, the present invention relates to a hybridization assay for detecting the presence of a target polynucleotide in a sample. According to the method, a CAP of the present invention is contacted with a sample of a nucleic acid under conditions favorable for hybridization. The fluorescence signal of the donor molecule is measured before and after being contacted with the sample. Since the donor molecule on the CAP exhibits a greater fluorescence signal when hybridized to a target sequence, an increase in the fluorescence signal after the CAP is contacted with the sample indicates the hybridization of the probe to target sequences in the sample and hence the presence of target sequences in the sample. Further, by quantifying the change in fluorescence intensity as a result of the probe being contacted with the sample, the amount of target sequences in the sample can be quantified.

According to one embodiment of the method, the conformationally assisted hybridization probe is immobilized on a solid support. The immobilized CAP is contacted with a sample of a nucleic acid under conditions favorable for hybridization. The fluorescence signal of the donor is measured before and after being contacted with the sample. Immobilization of the hybridization probe to the solid support enables the target sequence hybridized to the probe to be readily isolated from the sample. In later steps, the isolated target sequence may be separated from the solid support and processed (e.g., purified, amplified) according to methods well known in the art depending on the particular needs of the researcher.

In the methods described herein, unless otherwise noted, a preferred detector nucleic acid includes a single-stranded target binding sequence. The binding sequence has linked thereto: i) a fluorophore; and ii) a quencher. Moreover, prior to its hybridization to a complementary sequence, the detector nucleic acid is preferably in a conformation that allows donor-acceptor energy transfer between the fluorophore and the quencher when the fluorophore is excited. Furthermore, in each of the methods described in this section, a change in fluorescence is detected as an indication of the presence of the target sequence. The change in fluorescence is preferably detected in-real time.

Presently preferred nucleic acid probes do not require the carrier molecule to adopt a secondary structure for the probe to function.

In this method, and unless otherwise noted, the other methods described in this section, the detector nucleic acid can assume substantially any intramolecularly associated secondary structure, but this structure is preferably a member selected from hairpins, stem-loop structures, pseudoknots, triple helices and conformationally assisted structures. Moreover, the intramolecularly base-paired secondary structure preferably comprises a portion of the target binding sequence.

The CAP of the present invention may also be used as a probe for monitoring nucleic acid amplification. Accordingly, the present invention relates to a method for monitoring nucleic acid amplification using a CAP according to the present invention which is capable of hybridizing to the target sequence 3'-relative to an amplification primer. According to the method, nucleic acid amplification is performed on a target polynucleotide using a nucleic acid polymerase having 5→3'-nuclease activity, a primer capable of hybridizing to the target polynucleotide, and an CAP according to the present invention capable of hybridizing to the target polynucleotide 3'-relative to the primer. During amplification, the nucleic acid polymerase digests the CAP when it is hybridized to the target sequence, thereby separating the donor moiety from the acceptor moiety. As the amplification is conducted, the fluorescence of the donor molecule is monitored, the generation of fluorescence corresponding to the occurrence of nucleic acid amplification.

Use of a donor-acceptor pair probe in conjunction with the amplification of a target polynucleotide, for example, by PCR is described in many references, such as Innis et al., Eds, PCR Protocols (Academic Press, New York, 1989); Sambrook et al., Molecular Cloning, Second Edition (Cold Spring Harbor Laboratory, New York, 1989), each of which are incorporated herein by reference. The binding site of the CAP is located between the PCR primers used to amplify the target polynucleotide. Preferably, PCR is carried out using Taq DNA polymerase, e.g., Amplitaq TM (Perkin-Elmer, Norwalk, Conn.), or an equivalent thermostable DNA polymerase, and the annealing temperature of the PCR is about 5°–10° C. below the melting temperature of the oligonucleotide probes employed.

Use of a CAP according to the present invention for monitoring nucleic acid amplification provides several advantages over the use of prior art reporter-quencher pair probes. For example, prior art probes required that the reporter and quencher molecules be positioned on the probe such that the quencher molecule remained within a minimum quenching distance of the reporter molecule. However, by realizing that the probe need only be designed such that the probe be able to adopt a conformation where the quencher molecule is within a minimum quenching distance of the reporter molecule, a far wider array of probes are enabled. For example, dually labeled CAPs having the donor and acceptor molecules at the 5'- and 3'-ends can be designed. Such probes are generally easier to synthesize than probes where the reporter molecule or the quencher molecule is attached to an internal nucleotide. Moreover, positioning the donor and acceptor moieties on terminal nucleotides also enhances the hybridization efficiency of the CAPs.

In yet a further aspect, the invention provides a method of ascertaining whether a first nucleic acid and a second nucleic acid hybridize. In this method, the first nucleic acid is a CAP according to the invention. The method includes: (a) contacting the first nucleic acid with the second nucleic acid; (b) detecting an alteration in a fluorescent property of a member selected from the first nucleic acid, the second nucleic acid and a combination thereof, thereby ascertaining whether the hybridization occurs.

The nucleic acids for use in the probes of the invention can be any suitable size, and are preferably in the range of from about 10 to about 100 nucleotides, more preferably from about 10 to about 80 nucleotides and more preferably still, from about 20 to about 40 nucleotides. The precise sequence and length of a nucleic acid probe of the invention depends in part on the nature of the target polynucleotide to which it binds. The binding location and length may be varied to achieve appropriate annealing and melting properties for a particular embodiment. Guidance for making such design choices can be found in many art-recognized references.

Preferably, the 3'-terminal nucleotide of the nucleic acid probe is blocked or rendered incapable of extension by a nucleic acid polymerase. Such blocking is conveniently carried out by the attachment of a donor or acceptor moiety to the terminal 3'-position of the nucleic acid probe, either directly or by a linking moiety.

The nucleic acid can comprise DNA, RNA or chimeric mixtures or derivatives or modified versions thereof. Both the probe and target nucleic acid can be present as a single strand, duplex, triplex, etc. Moreover, the nucleic acid can be modified at the base moiety, sugar moiety, or phosphate backbone with other groups such as radioactive labels, minor groove binders, intercalating agents, donor and/or acceptor moieties and the like.

For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine.

In another embodiment, the nucleic acid comprises at least one modified sugar moiety selected from the group including, but not limited to, arabinose, 2-fluoroarabinose, xylulose, and hexose.

In yet another embodiment, the nucleic acid comprises at least one modified phosphate backbone selected from the group including, but not limited to, a peptide nucleic acid hybrid, a phosphorothioate, a phosphorodithioate, a phosphoramidothioate, a phosphoramidate, a phosphordiamidate, a methylphosphonate, an alkyl phosphotriester, and a formacetal or analog thereof.

Phosphodiester linked nucleic acids of the invention can be synthesized by standard methods known in the art, e.g. by use of an automated DNA synthesizer (such as are commercially available from P.E. Biosystems, etc.) using commercially available amidite chemistries. Nucleic acids bearing modified phosphodiester linking groups can be synthesized by methods known in the art. For example, phosphorothioate nucleic acids may be synthesized by the method of Stein et al. (*Nucl. Acids Res.* 16:3209 (1988)), methylphosphonate nucleic acids can be prepared by use of controlled pore glass polymer supports (Sarin et al., *Proc. Natl. Acad. Sci. U.S.A.* 85:7448–7451 (1988)). Other methods of synthesizing both phosphodiester- and modified phosphodiester-linked nucleic acids will be apparent to those of skill in the art.

Nucleic acid probes of the invention can be synthesized by a number of approaches, e.g., Ozaki et al., *Nucleic Acids Research*, 20: 5205–5214 (1992); Agrawal et al., *Nucleic Acids Research*, 18: 5419–5423 (1990); or the like. The nucleic acid probes of the invention are conveniently synthesized on an automated DNA synthesizer, e.g., a P.E. Biosystems, Inc. (Foster City, Calif.) model 392 or 394 DNA/RNA Synthesizer, using standard chemistries, such as phosphoramidite chemistry (see, for example, disclosed in the following references, Beaucage et al., *Tetrahedron*, 48: 2223–2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679. Alternative chemistries resulting in non-natural backbone groups, such as phosphorothioate, phosphoramidate, and the like, can also be employed.

When the nucleic acids are synthesized utilizing an automated nucleic acid synthesizer, the donor and acceptor moieties are preferably introduced during automated synthesis. Alternatively, one or more of these moieties can be introduced either before or after the automated synthesis procedure has commenced. For example, donor and/or acceptor groups can be introduced at the 3'-terminus using a solid support modified with the desired group(s). Additionally, donor and/or acceptor groups can be introduced at the 5'-terminus by, for example a derivative of the group that includes a phosphoramidite. In another exemplary embodiment, one or more of the donor and/or acceptor groups is introduced after the automated synthesis is complete.

In the dual labeled probes, the donor moiety is preferably separated from the acceptor by at least about 10 nucleotides, and more preferably by at least about 15 nucleotides. The donor moiety is preferably attached to either the 3'- or 5'-terminal nucleotides of the probe. The acceptor moiety is also preferably attached to either the 3'- or 5'-terminal nucleotides of the probe. More preferably, the donor and acceptor moieties are attached to the 3'- and 5'- or 5'- and 3'-terminal nucleotides of the probe, respectively, although internal placement is also useful.

Once the desired nucleic acid is synthesized, it is preferably cleaved from the solid support on which it was synthesized and treated, by methods known in the art, to remove any protecting groups present (e.g., 60° C., 5 h, concentrated ammonia). In those embodiments in which a base-sensitive group is attached to the nucleic acids (e.g., TAMRA), the deprotection will preferably use milder conditions (e.g., butylamine: water 1:3, 8 hours, 70° C.). Deprotection under these conditions is facilitated by the use of quick deprotect amidites (e.g., dC-acetyl, dG-dmf).

Following cleavage from the support and deprotection, the nucleic acid is purified by any method known in the art, including chromatography, extraction and gel purification. In a preferred embodiment, the nucleic acid is purified using HPLC. The concentration and purity of the isolated nucleic acid is preferably determined by measuring the optical density at 260 nm in a spectrophotometer.

5'-Nuclease Assay-Real Time Gene Quantitation

In another preferred embodiment, the present invention provides a modification of the Taqman assay in which one or more of the probes of the invention is utilized.

The ability to detect and quantitate gene targets rapidly, in real time, is now carried out routinely using the 5'-nuclease assay, often referred to as "Taqman" (FIG. 5). As the name implies, the process uses the 5'- to 3'-exonuclease activity of TAQ polymerase to digest a double labeled self quenched probe during the PCR amplification process. Typically, the probe is designed with a 5'-fluorescent reporter group and 3'-quencher, most often fluorescein and TAMRA, respectively. The Tm of the probe is selected to insure binding to the target under extension conditions (Tm ~65 C). Consequent digestion of the probe by TAQ polymerase generates free fluorophore each cycle of amplification, leading to exponential accumulation of fluorophore signal. By plotting the fluorescent signal vs. PCR cycle number and comparing with a standard reference curve, the number of starting gene copies can be determined. Thus, the assay determines both the presence of a gene as well as the amount of gene present. By using different probes with unique reporter fluorophores, several gene determinations can be performed simultaneously in the same reaction tube. As probes can be designed to discern a single base mismatch, specific alleles may be determined.

The power and utility of the 5'-nuclease assay has been expanded by the introduction of the ABI Prism 7700 Sequence Detector (Perkin Elmer) an instrument which automatically carries out the 5'-nuclease/PCR process in a 96 tube microtiter format. Since the tubes are closed throughout the process, contamination related by-products are precluded. The instrument monitors the fluorescence (at several wavelengths to allow multiplexing) in each well and software automatically plots data and determines gene copy numbers. A full analysis cycle providing 96 genetic data points (4×96 if multiplexed with four fluorophore probes) takes less than 2 hours. Since 386 tube thermocyclers have been released by ABI, it may be anticipated that the next generation will have the capability of reading this matrix of samples. Fluorophore multiplexing could in turn expand the number of assays possible to above 1000 per run. By prepacking standard primer pairs and probes into the tube wells, products for the rapid profiling of single-nucleotide polymorphisms (SNP) determinates or disease related genes could be produced. Such products would be valuable in the clinical genetics marketplace.

In spite of the remarkable power of the 5'-nuclease assay, some limitations prevent the widespread adaptation of the method. As reviewed previously, conventional FAM-TAM probes are often found to have inherent noise which limits their sensitivity. Part of the problem is the result of spurious fluorophoric by-products which can only be removed by the investment of significant purification expense. This results in high probe cost. However, the more serious limitation is derivative from the probe design itself which places the fluorophore and quencher at opposite ends of the probe. Since quenching is reduced dramatically with distance (inverse sixth power of the fluorophore/quencher separation) the FET phenomenon is effective only when fluorophore and quencher are within 100 Å. Since the separation of 5'-fluorophore and 3'-quencher of a 25-mer probe exceeds this distance, it might be predicted that no quenching should occur. That quenching does occur has been attributed to the flexibility of single stranded oligonucleotides which can bend sufficiently to allow conformations where the fluorophore and quencher are in close proximity.

In marked contrast, the CAPs of the invention produce very little background fluorescence. Thus, these CAPs are improved entities that are useful in the Taqman assay.

Use of Molecular Beacon-like CAPs

CAP analogues of molecular beacons are useful in a wide variety of important applications, including allelic discrimination and real-time PCR quantitation, and their selectivity is effective for distinguishing single base-pair mismatches. Thus, in another preferred embodiment, the present invention provides methods for performing these types of assays utilizing one or more CAPs.

In a preferred embodiment, the CAP-beacon is synthesized using 3'-DABCYL CPG. In this method, the full dual labeled probe in synthesized on the support, then deprotected and purified.

Peptide Probes

Peptides, proteins and peptide nucleic acids that are labeled with a fluorophore and a quencher of the invention can be used in both in vivo and in vitro enzymatic assays.

Thus, in another aspect, the present invention provides a method for determining whether a sample contains an enzyme. The method comprises: (a) contacting the sample with a peptide CAP probe; (b) exciting the fluorophore; and (c) determining a fluorescence property of the sample, wherein the presence of the enzyme in the sample results in a change in the fluorescence property.

Peptide constructs useful in practicing the invention include those with the following features: i) a molecular energy donor; ii) a molecular energy acceptor; and iii) a cleavage or assembly recognition site for the enzyme.

When the probe is used to detect an enzyme, such as a degradative enzyme (e.g., protease), and a degree of donor-acceptor energy transfer that is lower than an expected amount is observed, this is generally indicative of the presence of an enzyme. The degree of donor-acceptor energy transfer in the sample can be determined, for example, as a function of the amount of fluorescence from the donor moiety, the amount of fluorescence from the acceptor moiety, the ratio of the amount of fluorescence from the donor moiety to the amount of fluorescence from the acceptor moiety or the excitation state lifetime of the donor moiety.

The assay also is useful for determining the amount of enzyme in a sample by determining the degree of donor-acceptor energy transfer at a first and second time after contact between the enzyme and the tandem construct, and determining the difference in the degree of donor-acceptor energy transfer. The difference in the degree of donor-acceptor energy transfer reflects the amount of enzyme in the sample.

The assay methods also can also be used to determine whether a compound alters the activity of an enzyme, i.e., screening assays. Thus, in a further aspect, the invention provides methods of determining the amount of activity of an enzyme in a sample from an organism an exemplary method includes, for example: (a) contacting a sample comprising the enzyme and the compound with a CAP peptide construct comprising (b) exciting the fluorophore; and (c) determining a fluorescence property of the sample, wherein the activity of the enzyme in the sample results in a change in the fluorescence property. Peptide constructs useful in this aspect of the invention are substantially similar to those described immediately above.

In a preferred embodiment, the amount of enzyme activity in the sample is determined as a function of the degree of donor-acceptor energy transfer in the sample and the amount of activity in the sample is compared with a standard activity for the same amount of the enzyme. A difference between the amount of enzyme activity in the sample and the standard activity indicates that the compound alters the activity of the enzyme.

Representative enzymes with which the present invention can be practiced include, for example, trypsin, enterokinase, HIV-1 protease, prohormone convertase, interleukin-1b-converting enzyme, adenovirus endopeptidase, cytomegalovirus assemblin, leishmanolysin, β-secretase for amyloid precursor protein, thrombin, renin, angiotensin-converting enzyme, cathepsin-D and a kininogenase, and proteases in general.

Proteases play essential roles in many disease processes such as Alzheimer's, hypertension, inflammation, apoptosis, and AIDS. Compounds that block or enhance their activity have potential as therapeutic agents. Because the normal substrates of peptidases are linear peptides and because established procedures exist for making non-peptidic analogs, compounds that affect the activity of proteases are natural subjects of combinatorial chemistry. Screening compounds produced by combinatorial chemistry requires convenient enzymatic assays.

The most convenient assays for proteases are based on donor-acceptor energy transfer from a donor fluorophore to a quencher placed at opposite ends of a short peptide chain containing the potential cleavage site (see, Knight C. G., *Methods in Enzymol.* 248:18–34 (1995)). Proteolysis separates the fluorophore and quencher, resulting in increased intensity in the emission of the donor fluorophore. Existing protease assays use short peptide substrates incorporating unnatural chromophoric amino acids, assembled by solid phase peptide synthesis.

Assays of the invention are also useful for determining and characterizing substrate cleavage sequences of proteases or for identifying proteases, such as orphan proteases. In one embodiment the method involves the replacement of a defined linker moiety amino acid sequence with one that contains a randomized selection of amino acids. A library of fluorescent CAP peptide probes, consisting of randomized peptide linker moiety can be generated using recombinant engineering techniques or synthetic chemistry techniques. Screening the members of the library can be accomplished by measuring a signal related to cleavage, such as donor-acceptor energy transfer, after contacting the cleavage enzyme with each of the library members of the tandem fluorescent peptide construct. A degree of donor-acceptor energy transfer that is lower than an expected amount indicates the presence of a linker sequence that is cleaved by the enzyme. The degree of donor-acceptor energy transfer in the sample can be determined, for example, as a function of the amount of fluorescence from the donor moiety, the amount of fluorescence from the acceptor donor moiety, or the ratio of the amount of fluorescence from the donor moiety to the amount of fluorescence from the acceptor moiety or the excitation state lifetime of the donor moiety.

In the tandem constructs of the invention, the donor and acceptor moieties are connected through a linker moiety. The linker moiety, preferably, includes a peptide moiety, but can be or can include another organic molecular moiety, as well. In a preferred embodiment, the linker moiety includes a cleavage recognition site specific for an enzyme or other cleavage agent of interest. A cleavage site in the linker moiety is useful because when a tandem construct is mixed with the cleavage agent, the linker is a substrate for cleavage by the cleavage agent. Rupture of the linker moiety results in separation of the fluorophore and the quencher of the invention. The separation is measurable as a change in donor-acceptor energy transfer. Alternatively, peptide assembly can be detected by an increase in donor-acceptor energy transfer between a peptide fragment bearing an acceptor and a peptide fragment bearing a donor moiety.

When the cleavage agent of interest is a protease, the linker generally includes a peptide containing a cleavage recognition sequence for the protease. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in AMYLOID PROTEIN PRECURSOR IN DEVELOPMENT, AGING, AND ALZHEIMER'S DISEASE, ed. Masters et al. pp. 190–198 (1994).

Multiplex Analyses

In another preferred embodiment, one or more CAPs of the invention are utilized in a multiplex assay for detecting one or more species in a mixture.

CAPs of the invention are particularly useful in performing multiplex-type analyses and assays. In a typical multiplex analysis, two or more distinct species (or regions of one or more species) are detected using two or more probes, wherein each of the probes is labeled with a different fluorophore. Preferred species used in multiplex analyses relying on donor-acceptor energy transfer meet at least two criteria: the fluorescent species is bright and spectrally well-resolved; and the energy transfer between the fluorescent species and the quencher is efficient.

The CAPs of the invention allow for the design of multiplex assays in which more than one probe structure is used in the assay. Of particular advantage is that the biomolecule portion of the probe is not limited in structure to those sequences that form secondary structures. A number of different multiplex assays using the CAPs of the invention will be apparent to one of skill in the art. In one exemplary assay, at least two distinct CAPs is used to detect one or more components of a mixture.

The present invention also provides a method for detecting or quantifying a particular molecular species in a multiplex format using one or more CAPs. The method includes: (a) contacting the species with a mixture such as that described above; and (b) detecting a change in a fluorescent property of one or more component of the mixture, the molecular species or a combination thereof, thereby detecting or quantifying the molecular species.

The simultaneous use of two or more probes using donor-acceptor energy transfer is known in the art. For example, multiplex assays using nucleic acid probes with different sequence specificities have been described. Fluorescent probes have been used to determine whether an individual is homozygous wild-type, homozygous mutant or heterozygous for a particular mutation. For example, using one quenched-fluorescein molecular beacon that recognizes the wild-type sequence and another rhodamine-quenched molecular beacon that recognizes a mutant allele, it is possible to genotype individuals for the β-chemokine receptor (Kostrikis et al. *Science* 279:1228–1229 (1998)). The presence of only a fluorescein signal indicates that the individual is wild-type, and the presence of rhodamine signal only indicates that the individual is a homozygous mutant. The presence of both rhodamine and fluorescein signal is diagnostic of a heterozygote. Tyagi et al. *Nature Biotechnology* 16: 49–53 (1998)) have described the simultaneous use of four differently labeled molecular beacons for allele discrimination, and Lee et al., *Bio Techniques* 27: 342–349 (1999) have described seven color homogenous detection of six PCR products.

The CAPs of the present invention can be used in multiplex assays designed to detect and/or quantify substantially any species, including, for example, whole cells, viruses, proteins (e.g., enzymes, antibodies, receptors), glycoproteins, lipoproteins, subcellular particles, organisms (e.g., Salmonella), nucleic acids (e.g., DNA, RNA, and analogues thereof), polysaccharides, lipopolysaccharides, lipids, fatty acids, non-biological polymers and small molecules (e.g., toxins, drugs, pesticides, metabolites, hormones, alkaloids, steroids).

Additional Methods using CAPs

The above-described methods are set forth in some detail to illustrate the utility of CAPs in various procedures. Those of skill in the art will readily understand that these descriptions are not limiting, and that CAPs can be used in a variety of art-recognized methods. Exemplary methods include the use of CAPs as hairpin primers in PCR, allele specific PCR, triamplification, nucleic acid sequence-based amplification (NASBA), rolling circle amplification, strand displacement amplification and the like. The use of modified oligonucleotides in these amplification and assay formats is discussed in detail in, for example, U.S. Pat. No. 5,866,336, to Nazarene et al. on Feb. 2, 1999, the disclosure of which is incorporated herein by reference.

Kits for Detection and Amplification of Nucleic Acids

An additional aspect of the present invention relates to kits for the detection or measurement of nucleic acids and nucleic acid amplification products. In specific embodiments, the kits comprise one or more primer CAP oligonucleotides of the invention, such as a hairpin primer, including but not limited to a universal hairpin primer, and/or linear primers, in one or more containers. The kit can further comprise additional components for carrying out the amplification reactions of the invention. Where the target nucleic acid sequence being amplified is one implicated in disease or disorder, the kits can be used for diagnosis or prognosis. In a specific embodiment, a kit is provided that comprises, in one or more containers, forward and reverse primers of the invention for carrying out amplification, and optionally, a DNA polymerase or two DNA polymerases respectively with and without exonuclease activity. A kit for triamplification can further comprise, in one or more containers, a blocking oligonucleotide, and optionally DNA ligase.

Oligonucleotides in containers can be in any form, e.g., lyophilized, or in solution (e.g., a distilled water or buffered solution), etc. Oligonucleotides ready for use in the same amplification reaction can be combined in a single container or can be in separate containers. Multiplex kits are also provided, containing more than one pair of amplification (forward and reverse) primers, wherein the signal being detected from each amplified product is of a different wavelength, e.g., wherein the donor moiety of each primer pair fluoresces at a different wavelength. Such multiplex kits contain at least two such pairs of primers.

In a specific embodiment, a kit comprises, in one or more containers, a pair of primers preferably in the range of 10–100 or 10–80 nucleotides, and more preferably, in the range of 20–40 nucleotides, that are capable of priming amplification, e.g., by polymerase chain reaction (see, for example., Innis et al., PCR Protocols, Academic Press, Inc., San Diego, Calif. (1990)) by, for example, competitive PCR and competitive reverse-transcriptase PCR (Clement et al., Genet. Anal. Tech. Appl. 11(1): 1–6 (1994); Siegert et al., Nature 359:557–558 (1992); triamplification, NASBA, strand displacement, or other methods known in the art, under appropriate reaction conditions, of at least a portion of a selected target nucleic acid.

In another embodiment, a kit for the detection of a selected target DNA target sequence comprises in one or more containers (a) PCR primers, one or both of which are hairpin primers labeled with fluorescent and quenching moieties that can perform MET; and optionally: (b) a control DNA target sequence; (c) an optimized buffer for amplification; (d) appropriate enzymes for the method of amplification contemplated, e.g., a DNA polymerase for PCR or triamplification or SDA, a reverse transcriptase for NASBA; (d) a set of directions for carrying out amplification, e.g., describing the optimal conditions, e.g., temperature, number of cycles for amplification. Optionally, the kit provides (e) means for stimulating and detecting fluorescent light emissions, e.g., a fluorescence plate reader or a combination thermocycler-plate-reader to perform the analysis.

In yet another embodiment, a kit for triamplification is provided. The kit comprises forward and reverse extending primers, and a blocking oligonucleotide. Either the forward or reverse primer is labeled with one moiety of a pair of MET moieties, and the blocking oligonucleotide is labeled with the other MET moiety of the pair. One embodiment of such a kit comprises, in one or more containers: (a) a first oligonucleotide; (b) a second oligonucleotide, wherein said first and second oligonucleotides are linear primers for use in a triamplification reaction; (c) a third oligonucleotide that is a blocking oligonucleotide that comprises a sequence complementary and hybridizable to a sequence of said first oligonucleotide, said first and third oligonucleotides being labeled with a first and second moiety, respectively, that are members of a molecular energy transfer pair consisting of a donor moiety and an acceptor moiety, such that when said first and third oligonucleotides are hybridized to each other and the donor moiety is excited and emits energy, the acceptor moiety absorbs energy emitted by the donor moiety; and (d) in a separate container, a nucleic acid ligase.

Another embodiment of a kit comprises in a container a universal hairpin primer, optionally also comprising a second container containing cyanogen bromide or a nucleic acid ligase (e.g., DNA ligase, for example, T4 DNA ligase).

Another kit of the invention comprises in one or more containers: (a) a first oligonucleotide; (b) a second oligonucleotide, said first and second oligonucleotide being hybridizable to each other; said first oligonucleotide being labeled with a donor moiety said second oligonucleotide being labeled with an acceptor moiety, said donor and acceptor moieties being a molecular energy transfer pain, wherein the donor moiety emits energy of one or more particular wavelengths when excited, and the acceptor moiety absorbs energy at one or more particular wavelengths emitted by the donor moiety; and (c) in a separate container, a nucleic acid ligase.

The materials, methods and devices of the present invention are further illustrated by the examples which follow. These examples are offered to illustrate, but not to limit the claimed invention.

EXAMPLE 1

Example 1 details the synthesis of an exemplary CAP molecule. This CAP uses two cholesterol stabilizing groups, a fluorescein donor and a rhodamine acceptor. This CAP was found to have a substantially lower background fluorescence than an analogous probe with out the cholesterol stabilizing groups.

1.1 Materials and Methods

A model CAP probe was synthesized using cholesterol as the hydrophobic ligand. In this simple model, cholesterol units were placed adjacent to both the donor and acceptor. The model sequence was B-Actin which is a well characterized probe used in the "Taqman" gene quantitation system (ABI-Perkin-Elmer). Both probes were 5'-FAM, 3'-TAMRA labeled as follows:

Taqman Probe
5'-FAM-d5'CGCAGGATGGCATGGGGGAGGGCAT-TAMRA-3'

CAP Probe SEQ ID NO:2
5'-FAM-CHOL-d5'CGCAGGATGGCATGGGGGAGGGCAT-CHOL-TAMRA-3'

Each probe was synthesized on a Biosearch 8700 at the 0.200 or 1 micromole scale. 3'-TAMRA was introduced by prederivatized CPG (Biosearch). Cholesteryl moieties were added by the use of cholesteryl amidite (Glen Research). 5'-Fluorescein was added via 6-FAM amidite. Following synthesis, the TAMRA oligonucleotide was subjected to treatment at 70° C. for 8 hours in t-butylamine/water (⅓). Quick deprotect amidites (dC-acetyl; dG-dmf) were used when TAMRA oligos were prepared. The oligonucleotides not derivatized with TAMRA were treated at 60° C. for 5 hours in concentrated ammonia).

The oligonucleotides were rigorously purified by preparative PAGE and HPLC. Reverse phase HPLC analysis was carried out using a Beckman Ultrasphere XL column (3 μm particle, 4.6 mm by 7.6 cm.) on a Water's Millenium HPLC with 717 Autoinjector and 996 PDA array. Anion exchange was carried out on an identical system using Dionex AX column. In both cases, data was collected from 240 nm to 610 nm and the UV spectra extracted for major peak components.

The performance of the CAP probe was compared to a conventionally designed FET probe by exposing each probe to long wavelength UV to observe the degree of inherent background fluorescence. The degree of background fluorescence was quantitated by observing each probe in a spectrofluorometer (Molecular Devices; Gemini) at a 250 nM concentration and measuring the fluorescent signal.

Fluorescence measurements were carried out using a LS-50B Fluorescence, or SpectraMax Gemini fluorescence microplate reader. Both instruments excite and detect across a broad range of frequencies. Conditions: Probes in standard PCR buffer: 10 mM Tris-HCl, 50 mM KCl, 4 mM $MgCl_2$ Probe concentration 100 nM; Excitation for fluorescein 485 nm, emission measured at 518 nm and 582 nm for TAMRA. All measurements were taken in triplicate with the plate preread to eliminate background noise.

The difference in fluorescence output of each probe with and without a complementary hybridization target was also compared. Varying amounts of target were added to each probe type and the amount of fluorescence generated was measured. The fluorescein donor (D) group was excited at 485 nm and the acceptor emission signal was measured at 518 nm.

The emission of the acceptor (A), TAMRA, at 582 nm was measured. FET probe performance was assessed by examining the ratio of $D/A^-$ which is the ratio of donor to acceptor fluorescent emission with no target present, and $D/A^+$ which measures the fluorescent emission in the presence of target. The difference between the two $D/A^+$-minus $D/A^-$, or $\Delta$ (Delta) D/A, is a traditional measure of probe performance.

1.2 Results

The solution of the CAP probe showed no fluorescent signal. In contrast, the conventional the FAM/TAMRA probe produced a very noticeable green glow indicating compromised quenching. The results (Table 1) demonstrate that the FAM/TAM probe produces 8 times the fluorescent noise as the CAP probe. The CAP signal was very close to the expected background noise of the buffer/instrument.

TABLE 1

Comparison of Actin CAP probe with FAM/TAM Probe

|  | Probe w/o Compliment Fl Units 520 nm | Probe w/ Compliment Fl Units 520 nm | S/N |
|---|---|---|---|
| FAM-TAM Probe | 23.5 | 135 | 5.75 |
| CAP Probe | 3.2 | 101 | 31.56 |
| Control (Buffer Blank) | 2.1 | | |

Figure 2:
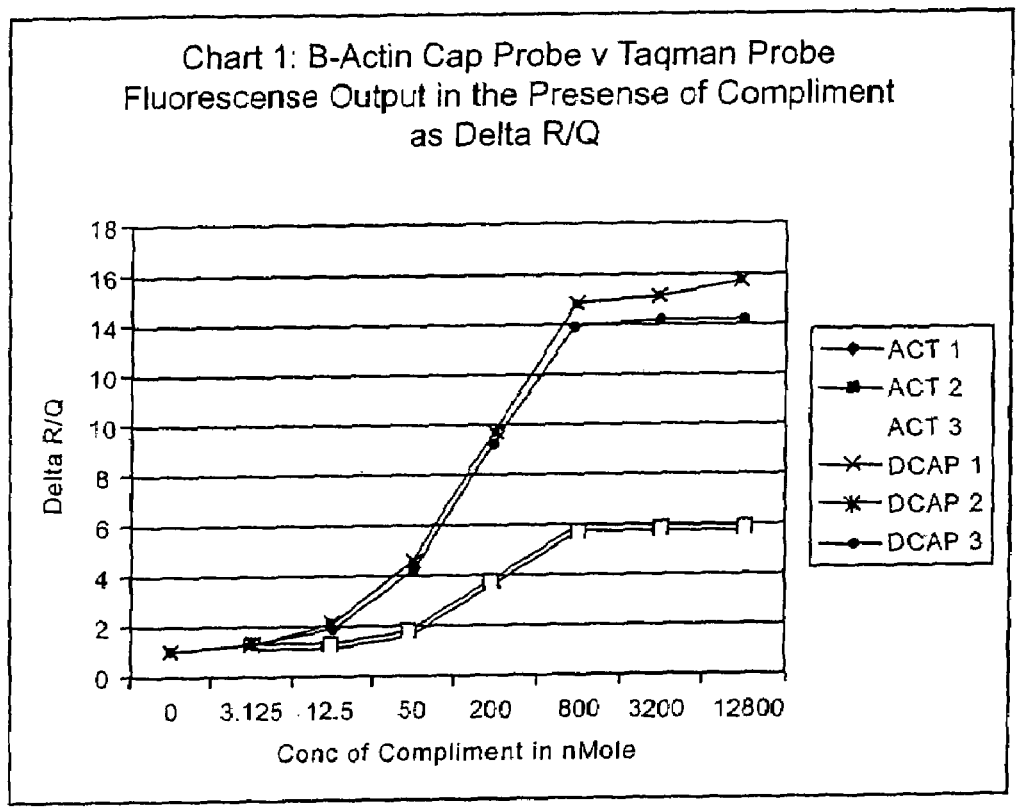
FIG. 2 is a plot of AR/Q vs. concentration of complement (nM) for an actin CAP probe and a Taqman probe.

Conditions: probe @ 250 nM; Compliment @ 2.5 um; PCR Buffer; RT Runs were done in triplicate In FIG. 2, the fluorescence output (measured as $\Delta$ D/A) of an Taqman probe is compared with the analogous CAP probe with cholesteryl ligands. The CAP probe fluorescent output ($\Delta$ D/A of 15) was significantly higher than the standard probe (A D/A 5.9).

Figure 3:
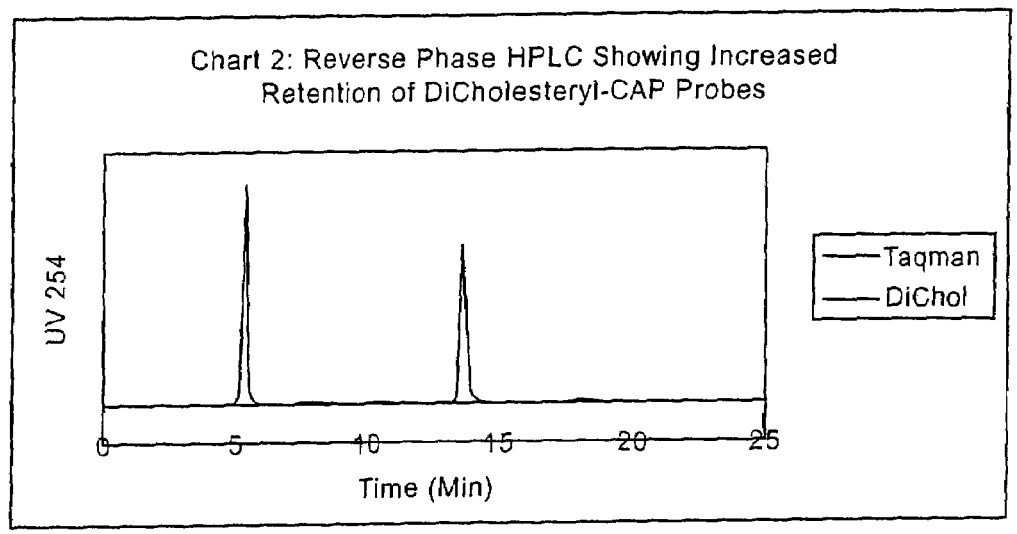
FIG. 3 is a reverse phase HPLC chromatogram showing the retention in this system of a dicholesteryl-CAP and Taqman probes.

FIG. 3 shows a reverse phase HPLC (Hamilton RP-1 column; 4.1 mm×250 mm) of B-Actin Taqman FAM/TAM probe (retention time 5 min) and the Dicholesteryl CAP analog (retention time 14 min).

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A probe nucleic acid having the formula:

$$D-R^1-Nu^1-R^2-O-\overset{\overset{O}{\|}}{\underset{O^-}{P}}-O-NA-O-\overset{\overset{O}{\|}}{\underset{O^-}{P}}-O-R^3-Nu^2-R^4-Q$$
$$\phantom{D-R^1-Nu^1-R^2-O-}\underset{CHOL}{|}\phantom{-O-NA-O-}\phantom{-O-}\underset{CHOL}{|}$$

wherein,

CHOL is a cholesterol derivative;

$R^1$, $R^2$, $R^3$ and $R^4$ are linker moieties independently selected from the group consisting of substituted or unsubstituted alkyl and substituted or unsubstituted heteroalkyl;

$Nu^1$ and $Nu^2$ are members independently selected from the group consisting of nucleotide residues and nucleoside residues;

NA is a nucleic acid sequence;

D is a donor of light energy; and

Q is a quencher of light energy, wherein the CHOL moieties interact to bring D and Q into position to enable transfer of energy from D to Q, and wherein said probe nucleic acid sequence is not hybridized to a target nucleic acid.

2. The probe nucleic acid according to claim 1, wherein $R^2$—CHOL and $R^3$—CHOL are independently selected and have structures according to the formula:

$$\begin{array}{c} -R^{11}- \\ | \\ PEG \\ | \\ Y^3 \\ | \\ CHOL \end{array}$$

wherein, $R^{11}$ is a member selected from the group consisting of substituted or unsubstituted alkyl and substituted or unsubstituted heteroalkyl;

PEG is polyethylene glycol;

$Y^3$ is an organic functional group adjoining said PEG to said CHOL.

3. The probe nucleic acid according to claim 2, wherein said PEG has from about 2 to about 20 ethylene glycol subunits.

4. The probe nucleic acid according to claim 2 in which $R^{11}$ is substituted or unsubstituted alkyl.

5. The probe nucleic acid according to claim 3, wherein $R^{11}$ is $C_1$–$C_6$ substituted or unsubstituted alkyl.

6. The probe nucleic acid according to claim 2, wherein $Y^3$—CHOL has the structure:

[structure of cholesterol carbamate: —NHC(O)O-cholesteryl]

7. The probe nucleic acid according to claim 1, 2 wherein $Nu^1$ and $Nu^2$ are nucleotides having an exocyclic amine group to which —$R^1$—D and —$R^4$Q are attached, respectively.

8. A probe nucleic acid having the formula:

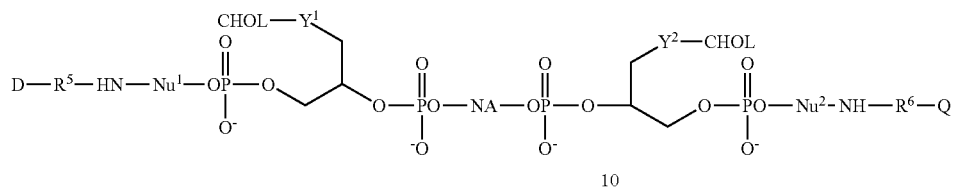

wherein,
- NA is a nucleic acid sequence;
- $Nu^1$ and $Nu^2$ are members independently selected from the group consisting of nucleotide residues and nucleoside residues;
- $Y^1$ and $Y^2$ are linking groups independently selected from the group consisting of substituted or unsubstituted alkyl and substituted or unsubstituted heteroalkyl;
- $R^5$ and $R^6$ are linking groups independently selected from the group consisting of substituted or unsubstituted alkyl and substituted or unsubstituted heteroalkyl;
- D is a donor of light energy; and
- Q is a quencher of light energy,
- wherein the CHOL moieties interact to bring D and Q into position to enable transfer of energy from D to Q, and
- wherein said probe nucleic acid sequence is not hybridized to a target nucleic acid.

9. The probe nucleic acid according to claim 8, wherein $Y^1$ and $Y^2$ are members independently selected from substituted or unsubstituted heteroalkyl.

10. The probe nucleic acid according to claim 9, wherein $Y^1$ and $Y^2$ are polyethylene glycol.

11. The probe nucleic acid according to claim 10, wherein said polyethylene glycol has from about 2 to about 20 ethylene glycol subunits.

12. The probe nucleic acid according to claim 8, wherein $Y^1$—CHOL and $Y^2$—CHOL have the structure:

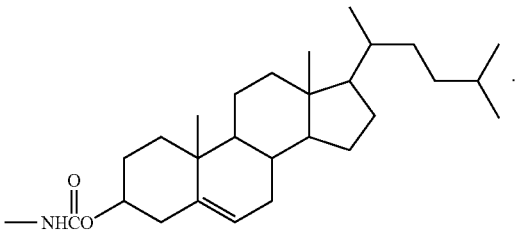

* * * * *

UNITED STATES PATENT AND TRADEMARK OFFICE
CERTIFICATE OF CORRECTION

PATENT NO. : 7,160,996 B1
APPLICATION NO. : 09/591185
DATED : January 9, 2007
INVENTOR(S) : Ronald M. Cook Page 1 of 1

It is certified that error appears in the above-identified patent and that said Letters Patent is hereby corrected as shown below:

On the first page of the patent, left column, at line "(73)" please change assignee's name from "Bioresearch Technologies, Inc." to --Biosearch Technologies, Inc.--.

Signed and Sealed this

First Day of June, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:"TaqMan"
      probe
<221> NAME/KEY: modified_base
<222> LOCATION: (1)
<223> OTHER INFORMATION: n = cytosine modified through a substituted or
      unsubstituted alkyl or heteroalkyl linking group
      by exemplary donor 5-carboxyfluorescein (FAM)
<221> NAME/KEY: modified_base
<222> LOCATION: (25)
<223> OTHER INFORMATION: n = thymine modified through a substituted or
      unsubstituted alkyl or heteroalkyl linking group
      by exemplary acceptor
      N,N,N',N'-tetramethyl-6-carboxyrhodamine (TAMRA)

<400> SEQUENCE: 1
ngcaggatgg catgggggag ggcan                                           25

<210> SEQ ID NO 2
<211> LENGTH: 25
<212> TYPE: DNA
<213> ORGANISM: Artificial Sequence
<220> FEATURE:
```

-continued

```
<223> OTHER INFORMATION: Description of Artificial Sequence:model
      conformationally assisted probe (CAP)
<221> NAME/KEY: modified_base
<222> LOCATION: (1)
<223> OTHER INFORMATION: n = cytosine modified through a substituted or
      unsubstituted alkyl or heteroalkyl linking group
      by exemplary donor 5-carboxyfluorescein (FAM)
<221> NAME/KEY: modified_base
<222> LOCATION: (2)
<223> OTHER INFORMATION: n = guanine modified through a substituted or
      unsubstituted alkyl or heteroalkyl linking group
      by exemplary stabilizing moiety cholesterol
      derivative (CHOL)
<221> NAME/KEY: modified_base
<222> LOCATION: (24)
<223> OTHER INFORMATION: n = adenine modified through a substituted or
      unsubstituted alkyl or heteroalkyl linking group
      by exemplary stabilizing moiety cholesterol
      derivative (CHOL)
<221> NAME/KEY: modified_base
<222> LOCATION: (25)
<223> OTHER INFORMATION: n = thymine modified through a substituted or
      unsubstituted alkyl or heteroalkyl linking group
      by exemplary acceptor
      N,N,N',N'-tetramethyl-6-carboxyrhodamine (TAMRA)

<400> SEQUENCE: 2
nncaggatgg catgggggag ggcnn                                           25
```